(12) United States Patent
Rotman et al.

(10) Patent No.: US 10,080,838 B2
(45) Date of Patent: Sep. 25, 2018

(54) CATHETER CANNULA WITH ANCHORING ELEMENTS, CATHETER INCLUDING THEREOF, AND/OR CATHETERIZATION METHOD USING THEREOF

(75) Inventors: Oren Rotman, Holon (IL); Shmuel Einav, Herzlia (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 659 days.

(21) Appl. No.: 13/809,941

(22) PCT Filed: Jul. 12, 2011

(86) PCT No.: PCT/IL2011/000553
§ 371 (c)(1),
(2), (4) Date: Jan. 14, 2013

(87) PCT Pub. No.: WO2012/007944
PCT Pub. Date: Jan. 19, 2012

(65) Prior Publication Data
US 2013/0116652 A1    May 9, 2013

Related U.S. Application Data

(60) Provisional application No. 61/363,309, filed on Jul. 12, 2010.

(51) Int. Cl.
*A61M 5/158* (2006.01)
*A61M 25/04* (2006.01)
(Continued)

(52) U.S. Cl.
CPC .......... *A61M 5/158* (2013.01); *A61M 25/04* (2013.01); *A61M 25/065* (2013.01);
(Continued)

(58) Field of Classification Search
CPC .......... A61M 25/02; A61M 2025/0233; A61M 25/04; A61M 2025/0008; A61M 25/0105; A61B 2017/3484
See application file for complete search history.

(56) References Cited

U.S. PATENT DOCUMENTS 3,654,932 A * 4/1972 Newkirk ............ A61M 27/006
604/185
3,674,033 A * 7/1972 Powers ................ A61M 25/02
138/114

(Continued)

FOREIGN PATENT DOCUMENTS

CN      101252958        8/2008
DE      102004035987     2/2006
(Continued)

OTHER PUBLICATIONS

International Search Report and the Written Opinion dated Dec. 6, 2011 From the International Searching Authority Re. Application No. PCT/IL2011/000553.
(Continued)

*Primary Examiner* — Bradley J Osinski
*Assistant Examiner* — Nilay Shah

(57) ABSTRACT

Catheter cannula, catheter, and catheterization method, for administering a fluid or/and substance to, or for draining a fluid or/and substance from, a treatment space of a body vessel, duct, or cavity. In some embodiments the cannula includes: an elongated flexible tube mountable on a needle, and having an invasive section and a non-invasive section; and at least one anchoring element protruding from, a surface of the invasive section in a manner such that an operative configuration of each anchoring element increases outer circumferential diameter of the cannula to an extent less than lumen diameter of the body vessel, duct, or cavity, at the treatment space, thereby anchoring the invasive sec-
(Continued)

tion to inside the body vessel, duct, or cavity, at the treatment space. The catheter includes a needle and the cannula mounted thereupon.

40 Claims, 20 Drawing Sheets

(51) Int. Cl.
    *A61M 25/06* (2006.01)
    *A61M 27/00* (2006.01)
    *A61M 25/00* (2006.01)
    *A61M 25/02* (2006.01)
    *A61B 17/34* (2006.01)

(52) U.S. Cl.
    CPC ..... *A61M 27/00* (2013.01); *A61B 2017/3484* (2013.01); *A61M 25/02* (2013.01); *A61M 2025/0008* (2013.01)

(56) References Cited

U.S. PATENT DOCUMENTS

| | | | | |
|---|---|---|---|---|
| 3,788,327 | A * | 1/1974 | Donowitz | A61B 3/16 604/175 |
| 3,896,804 | A * | 7/1975 | Ekbladh | A61M 25/04 604/174 |
| 4,114,618 | A | 9/1978 | Vargas | |
| 4,671,291 | A * | 6/1987 | Wilson | A61M 25/0108 600/435 |
| 5,052,998 | A * | 10/1991 | Zimmon | A61F 2/94 604/530 |
| 5,256,146 | A | 10/1993 | Ensminger et al. | |
| 5,257,975 | A * | 11/1993 | Foshee | A61B 17/34 604/105 |
| 5,391,159 | A * | 2/1995 | Hirsch | A61J 15/0019 604/175 |
| 5,509,900 | A | 4/1996 | Kirkman et al. | |
| 5,611,778 | A * | 3/1997 | Brinon | A61M 25/01 604/117 |
| 5,755,697 | A | 5/1998 | Jones et al. | |
| 5,984,896 | A | 11/1999 | Boyd | |
| 6,134,467 | A * | 10/2000 | Ouchi | A61B 18/1477 604/164.01 |
| 6,162,221 | A | 12/2000 | Ouchi | |
| 6,221,060 | B1 * | 4/2001 | Willard | A61M 25/0075 600/29 |
| 6,451,042 | B1 * | 9/2002 | Bonutti | A61B 17/0218 600/204 |
| 7,377,897 | B1 | 5/2008 | Kunkel et al. | |
| 2005/0256458 | A1 | 11/2005 | Howard et al. | |
| 2007/0106319 | A1 * | 5/2007 | Au | A61B 17/34 606/191 |
| 2008/0255475 | A1 * | 10/2008 | Kondrosky | A61M 25/09 600/585 |
| 2008/0287908 | A1 | 11/2008 | Muni et al. | |
| 2008/0312599 | A1 | 12/2008 | Rosenberg | |
| 2010/0145278 | A1 | 6/2010 | Magana | |

FOREIGN PATENT DOCUMENTS

| | | |
|---|---|---|
| EP | 0931559 | 7/1999 |
| WO | WO 91/15254 | 10/1991 |
| WO | WO 95/10317 | 4/1995 |
| WO | WO 99/08741 | 2/1999 |
| WO | WO 2007/103999 | 9/2007 |
| WO | WO 2009/011993 | 1/2009 |
| WO | WO 2012/007944 | 1/2012 |

OTHER PUBLICATIONS

International Preliminary Report on Patentability dated Jan. 24, 2013 From the International Bureau of WIPO Re. Application No. PCT/IL2011/000553.
Notification of Office Action dated Jun. 9, 2014 From The State Intellectual Property Office of the People's Republic of China Re. Application No. 2011800438646 and Its Translation Into English.
Search Report dated Jun. 9, 2014 From The State Intellectual Property Office of the People's Republic of China Re. Application No. 2011800438646 and Its Translation Into English.
Rotman "Short Peripheral Catheter Thrombophlebitis", Literature Review, Part of Master of Science Research, p. 1-10., Nov. 17, 2009.
Communication Pursuant to Article 94(3) EPC dated May 24, 2018 From the European Patent Office Re. Application No. 11749251.2. (6 Pages).

* cited by examiner

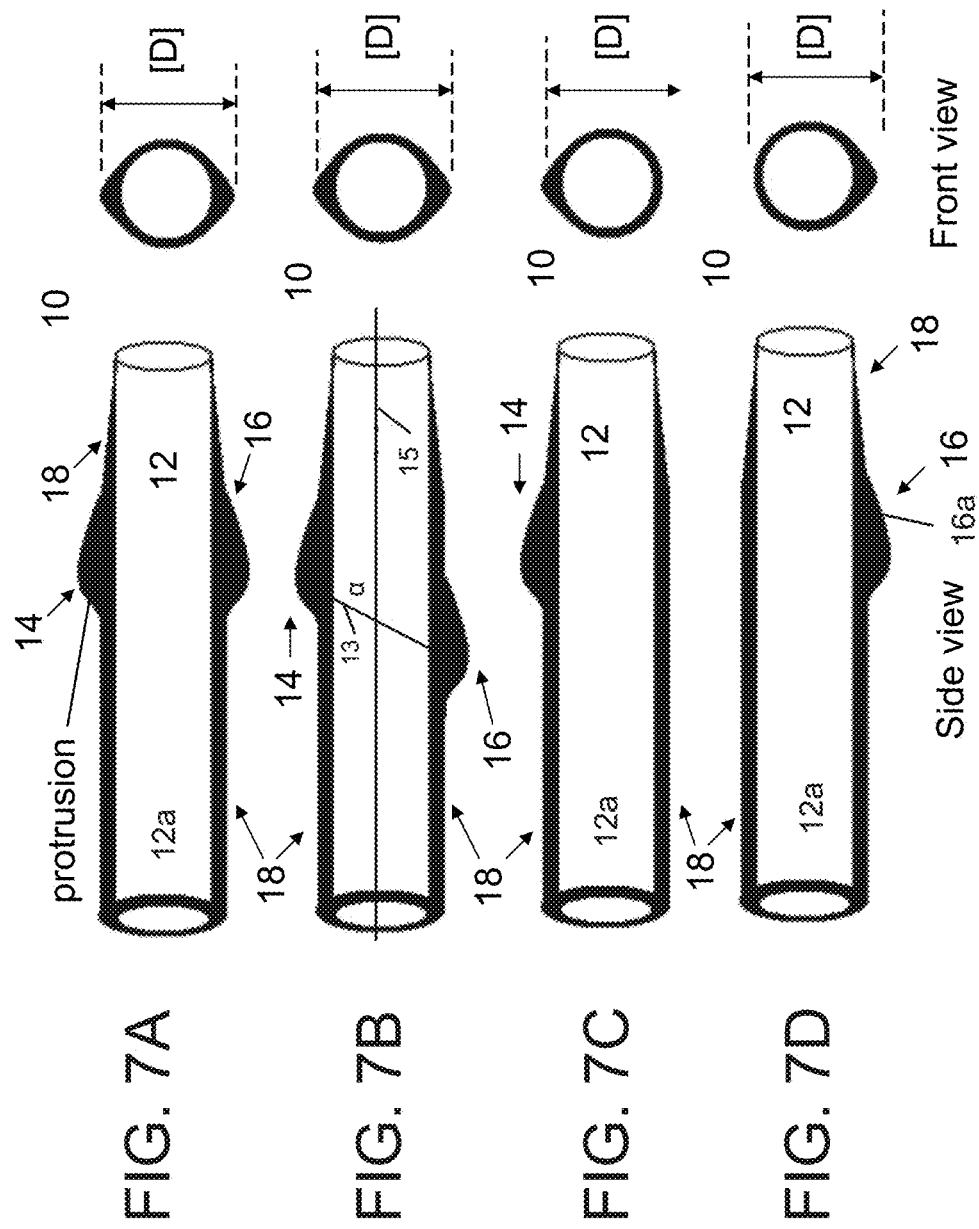

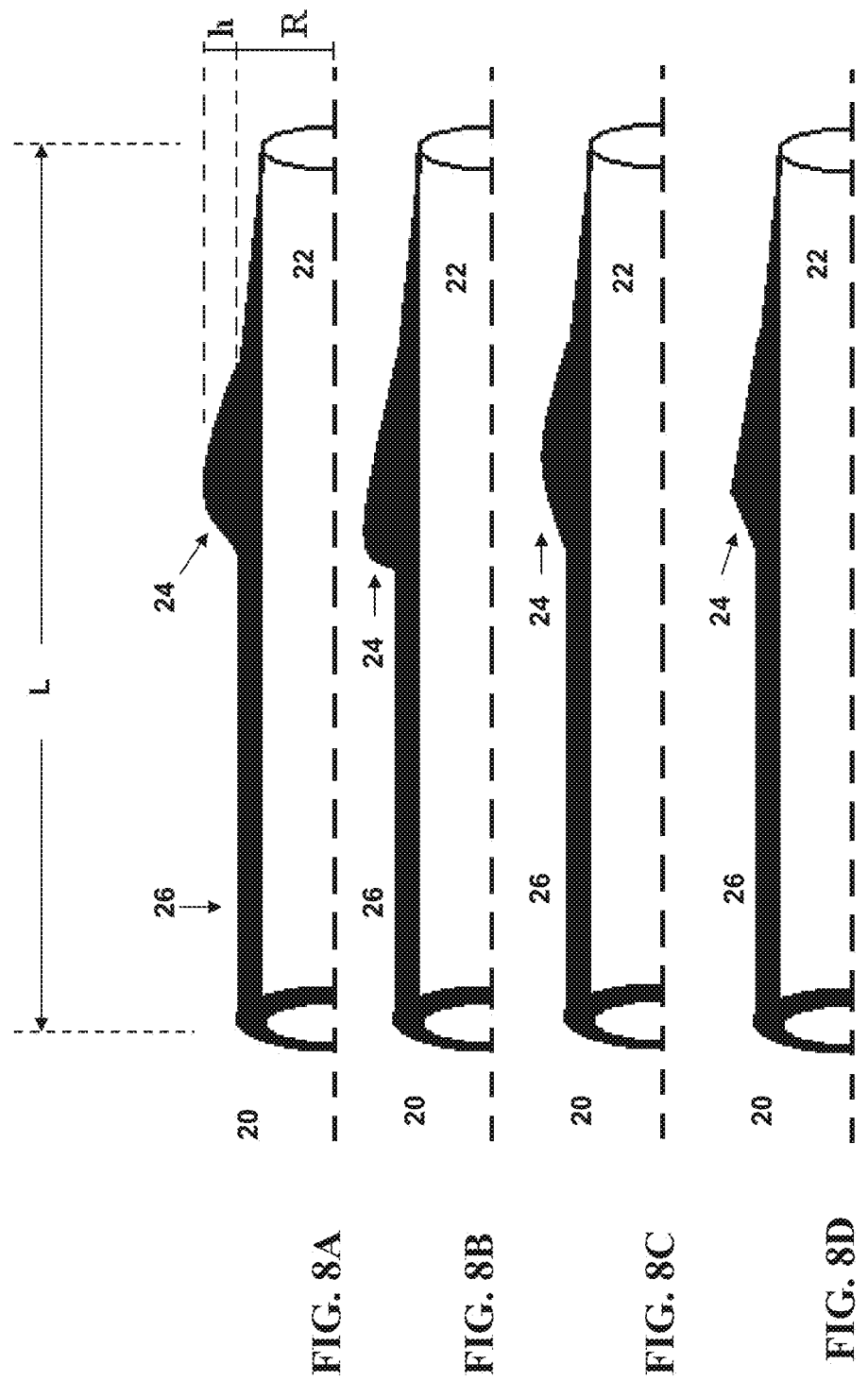

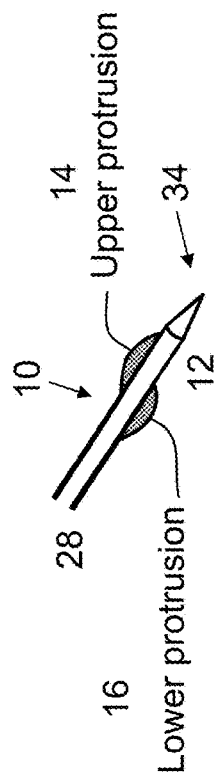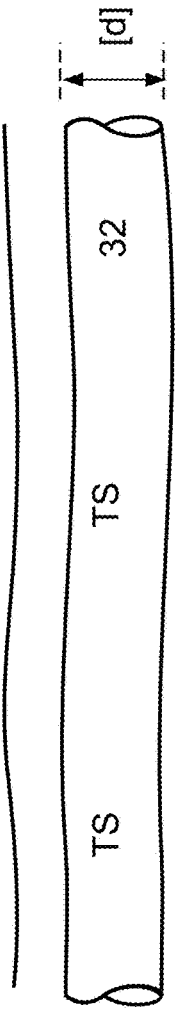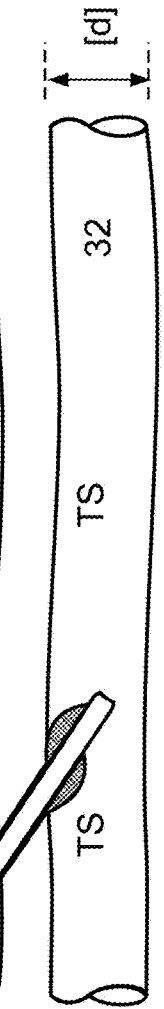
FIG. 9A
FIG. 9B
FIG. 9C

CATHETER CANNULA WITH ANCHORING ELEMENTS, CATHETER INCLUDING THEREOF, AND/OR CATHETERIZATION METHOD USING THEREOF

This application is a National Phase of PCT Patent Application No. PCT/IL2011/000553 having International filing date of Jul. 12, 2011, which claims the benefit of priority under 35 USC § 119(e) of U.S. Provisional Patent Application No. 61/363,309, filed Jul. 12, 2010. The contents of the above applications are all incorporated by reference as if fully set forth herein in their entirety.

FIELD AND BACKGROUND OF THE INVENTION

The present invention, in some embodiments thereof, relates to catheter cannulas (cannulas), catheters, and catheterization methods, and, more particularly, but not exclusively, to a cannula, a catheter, and a (catheterization) method, for administering a fluid or/and substance to, or for draining a fluid or/and substance from, a treatment space of a body vessel, duct, or cavity, for example, a vein or an artery. Exemplary fluids or/and substances are drugs, infusion therapy products, and blood products.

In various interventional medical procedures it is desirable to place a catheter within a patient's blood vessel for purposes of infusion of drugs or fluids, and/or for withdrawing blood. Most commonly, such catheters are first inserted into a blood vessel, and then connected to a supply container for the introduction of fluid by gravity flow or under positive pressure into the vessel.

Vascular access with catheters was introduced more than 100 years ago. It is well known in the medical field that chronic placement of a catheter in a patient's blood vessel often results in catheter failure due to aspiration of the blood vessel wall into the tip of the catheter, clot or thrombus formation at the tip of the catheter, local inflammation, e.g. phlebitis or thrombophlebitis and/or stenosis around the tip of the catheter. A catheter failure resulting from one or more of these mechanisms is evidenced by the inability to aspirate and/or infuse fluid through the catheter, commonly known as catheter occlusion. Typically, catheter occlusions caused by aspiration of the blood vessel wall or clot formation at the catheter tip may be resolved by repositioning the catheter tip or infusing antithrombotic agents.

Some progress has been made in this regard. Following are several exemplary teachings of various designs of catheter apparatuses that address issues of catheter dislodgement, or/and their inability to aspirate, or/and infuse fluid through the catheter.

US Pat. Appl. Pub. No. 2008/0312599 A1 relates to a catheter apparatus that resides in a fixed position within a blood vessel. As shown in FIG. 1, the catheter apparatus 100 has anchoring elements 160 and 161 which are pulled out when the handle 170 is pulled. Possible limitations or disadvantages of this invention are twofold: (1) design of the catheter is such that the anchoring elements apparently contact two points of the vessel wall, and (2) the anchoring mechanism requires a considerable reduction of the diameter of the catheter lumen 200, translating to reduction in possible maximum flow rates of liquids through the catheter.

US Pat. Appl. Pub. No. 2005/0256458 A1 relates to a catheter apparatus with anchoring elements, located on the hub or the catheter itself. As shown in FIG. 2, the anchoring elements 115 are opened and closed with a twisting motion of a hub 110. The anchoring elements 115 outwardly extend from the catheter outer surface and get stuck (like spikes) in adjacent tissue or skin, thereby preventing dislodgement of the catheter from its intended location. The anchoring is non-specific to the vessel lumen, but to essentially all tissue along the catheter body.

U.S. Pat. No. 5,256,146 relates to an implantable vascular catheterization system incorporating an anchoring mechanism including one or more anchoring elements for maintaining the tip of an implanted catheter at a desired position within the blood vessel. As shown in FIG. 3, each anchoring element (14, 34, 40, 42) is a flexible wire which outwardly extends from the catheter tip, and expands to contact and fit the vessel wall 24. The anchoring mechanism is based on increased contact with the vessel wall, involving increasing pressure on the vessel wall for increasing the grip thereupon.

U.S. Pat. No. 4,114,618 relates to a catheter assembly, including an anchoring flap, that is inserted into a blood vessel for directing medicinal fluids intravenously into the vessel. As shown in FIG. 4, the anchoring flap 39 is mountable onto the catheter assembly for anchoring the catheter. Contact between the catheter and the vein wall, via the flap 39, appears to increase rather than be eliminated.

U.S. Pat. No. 5,509,900 relates to a method and apparatus for retaining a catheter tip in a fixed position within a blood flow and preventing it from contacting a blood vessel wall. As shown in FIG. 5, the apparatus includes anchoring (tip retainer) elements 12 at the distal end of the catheter, for anchoring the tip of the catheter within a blood vessel. The disclosed invention aims to reduce damage to the vein wall 25, 26 by eliminating relative movement between the catheter tip and the vein wall. However, this is achieved by applying pressure and possibly damaging the vessel wall using the anchoring elements WO 2003/080166 relates to a venous port in which one or more extensions are provided which can selectively remove impediments from an aperture of the port.

SUMMARY OF THE INVENTION

The present invention, in some embodiments thereof, relates to catheter cannulas (cannulas), catheters, and catheterization methods, and, more particularly, but not exclusively, to a cannula, a catheter, and/or a (catheterization) method, for administering a fluid or/and substance to, or for draining a fluid or/and substance from, a treatment space of a body vessel, duct, or cavity. Exemplary fluids or/and substances are drugs, infusion therapy products, and blood products.

An aspect of some embodiments of the invention of the invention relates to a catheter with an anchoring mechanism, in which the mechanism increases the catheter external cross-section so as to reduce likelihood of pull-out, while avoiding or reducing contact with the vessel wall. In an exemplary embodiment of the invention, the reduced contact includes avoiding applying force to two opposing sides of the vessel such that the vessel is distorted by the applied force. Optionally or alternatively, the reduced contact includes not piercing the vessel wall with wall damaging elements.

In an exemplary embodiment of the invention, the anchoring mechanism includes a protrusion on a tube of the catheter which is used for fluid communication between the vessel and the outside of the body. Optionally, the protrusion is fixed. Optionally, such a protrusion is axially asymmetric, in that it has a sloped leading edge to assist in insertion and a more abrupt trailing edge, to assist in preventing removal. While the trailing edge may have an angle of, for example, 60 degrees with respect to the catheter surface, other angles, such as 90 degrees (perpendicular) and 120 degrees (undercut) may be provided. Optionally, the protrusion is at least partially spirally laid along the catheter so that rotation may be used to aid in insertion and/or removable.

In some embodiments of the invention, the protrusion changes shape during before and/or after insertion. Optionally, an overtube is provided to control the shape of the protrusion during insertion. Optionally, there is no extant protrusion during insertion. In an exemplary embodiment of the invention, the shape and/or position of the protrusions are controlled from outside the body, for example, using the overtube, for example, axially sliding and/or rotating the overtube to reveal a protrusion so it can extend radially.

In an exemplary embodiment of the invention, the protrusion provides only a small increase in maximum diameter to the catheter, for example, 20%, 30%, 40%, 50% or smaller, intermediate or larger percentages. Optionally, the increase is at least 5%, 10%, 20% or intermediate increases.

There is provided in accordance with an exemplary embodiment of the invention, a cannula for fluid exchange with a body lumen, the cannula comprising:

an elongated flexible tube coupleable to a needle, and having an invasive section and a non-invasive section and defining a lumen for fluid transfer; and at least one anchoring element integral with said tube and adapted to radially extend away from said tube.

In an exemplary embodiment of the invention, said radial extension is less than 30% of an outer diameter of said tube other than at an anchoring element location. Optionally, said radial extension is less than 50% of an outer diameter of said tube other than at an anchoring element location.

In an exemplary embodiment of the invention, said anchoring element is permanently protruding. Optionally, said at least one anchoring element is mounted on the external surface of a rear portion of said invasive section, said at least one anchoring element extends the cross section area of rear portion in relation to the cross section area of a front portion of said invasive section.

In an exemplary embodiment of the invention, said anchoring element has a leading slope gentler than a trailing slope thereof.

In an exemplary embodiment of the invention, said anchoring element has two configurations, one where it is radially compressed and one where it radially extends. Optionally, said anchoring element is an axial extension of said tube. Optionally, said anchoring element comprises a plurality of extensions of said tube pre-disposed to curl outwards away from said tube when release. Optionally or alternatively, said anchoring element comprises at least one extension said tube pre-disposed to bend outwards away from said tube when release.

In an exemplary embodiment of the invention, said anchoring element comprises a distortion of a wall of said tube.

In an exemplary embodiment of the invention, the cannula comprises an over tube which radially compresses said anchoring element. Optionally, said overtube is axially and/or rotationally manipulateable from said non-invasive section. Optionally or alternatively, said overtube and said anchor element are formed of a same material.

In an exemplary embodiment of the invention, said overtube and said anchor element are formed different materials.

In an exemplary embodiment of the invention, said at least one anchoring element is narrowing toward said front portion.

In an exemplary embodiment of the invention, said at least one anchoring element has a radial dimension smaller than an outer diameter of said elongated flexible tube.

In an exemplary embodiment of the invention, said at least one anchoring element has circumferential extent of less than 30% of a circumference of said tube.

In an exemplary embodiment of the invention, said at least one anchoring element has a circumferential extent of less than 50% of a circumference of said tube.

In an exemplary embodiment of the invention, said elongated flexible tube and said at least one anchoring element are made from a common material.

In an exemplary embodiment of the invention, said elongated flexible tube and said at least one anchoring element are integrally formed. Optionally, said at least one anchoring element and said invasive section are molded as a single piece.

In an exemplary embodiment of the invention, said at least one anchoring element is a detachable element.

In an exemplary embodiment of the invention, said anchoring element is formed of a material soft enough and not including edges sharp enough to damage vein vessel walls.

In an exemplary embodiment of the invention, said anchoring element is formed of a flexible polymeric material.

In an exemplary embodiment of the invention, the cannula is mounted on a needle to form a catheter. Optionally, said elongated flexible tube concentrically surrounds said needle.

In an exemplary embodiment of the invention, said at least one anchoring element comprising a plurality of axially spaced apart anchoring protrusions.

In an exemplary embodiment of the invention, said at least one anchoring element comprising a plurality of circumferentially spaced apart anchoring protrusions.

In an exemplary embodiment of the invention, said at least one anchoring element is asymmetrically arranged with respect to said cannula longitudinal axis. Optionally, said anchoring element comprises a first anchoring element closer to a top of said cannula and a second element further from said tip of said cannula.

In an exemplary embodiment of the invention, the ratio between the outer diameter of said elongated flexible tube and length of said elongated flexible tube is at least 0.07.

In an exemplary embodiment of the invention, the cannula is used for administering a fluid or/and substance to, or for draining a fluid or/and substance from, a treatment space of a body vessel, duct, or cavity and said anchoring element protrudes from a surface of the invasive section of said tube in a manner such that an operative configuration of said at least one anchoring element increases outer circumferential diameter of the cannula to an extent less than lumen diameter of the treatment space, thereby anchoring said invasive section to inside the body vessel, duct, or cavity, at the treatment space.

In an exemplary embodiment of the invention, said anchoring element comprises a protrusion which has a radial extent large enough to interfere with an inadvertent retraction of said cannula from a vessel in which it is placed.

There is provided in accordance with an exemplary embodiment of the invention, a method of fluid exchange with a body lumen, comprising:

inserting at least part of an invasive section of a cannula into said lumen via an aperture into said space, wherein said cannula is configured as an elongated flexible tube having an invasive section and a non-invasive section, and having at least one anchoring element associated with said invasive section;

preventing retraction of said cannula from said aperture by said anchoring element mechanically interfering with said aperture; and administering the fluid or/and substance to, or draining the fluid or/and substance from, a treatment space of the body vessel, duct, or cavity, via said cannula. Optionally, the method further comprising inserting said cannula using an insertion needle and retracting said needle from said elongated flexible tube before said administering.

Optionally, the method causing said anchoring element to extend away from said cannula after its insertion. Optionally, said causing comprises causing by manipulation from outside said body.

In an exemplary embodiment of the invention, said inserting and said preventing comprise avoiding applying a distorting force to two opposing walls of said lumen.

In an exemplary embodiment of the invention, said inserting and said preventing comprise avoiding damaging a portion of a wall of said space other than adjacent said aperture.

In an exemplary embodiment of the invention, said inserting and said preventing comprise not allowing said cannula to have a outer diameter equal to or greater than said vessel.

In an exemplary embodiment of the invention, said inserting and said preventing comprise not allowing said cannula to have an outer diameter greater than 130% of an inner diameter thereof.

In an exemplary embodiment of the invention, said lumen is a vein lumen. Optionally, said inserting and said preventing comprise avoiding contacting a wall of said vein that is opposite said aperture.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7A is a schematic diagram illustrating side and front views of an exemplary embodiment of the cannula whose invasive section includes two anchoring elements protruding from the outer surface thereof, wherein the anchoring elements are, for example, diametrically (180°) oppositely positioned relative to each other on upper and lower portions of the outer surface of the invasive section, in accordance with an exemplary embodiment of the present invention;

FIG. 7B is a schematic diagram illustrating side and front views of an exemplary embodiment of the cannula whose invasive section includes two anchoring elements protruding from the outer surface thereof, wherein the anchoring elements are, for example, diagonally (180°) oppositely positioned relative to each other on upper and lower portions of the outer surface of the invasive section, in accordance with an exemplary embodiment of the present invention;

FIG. 7C is a schematic diagram illustrating side and front views of an exemplary embodiment of the cannula whose invasive section includes one anchoring element protruding from the (upper portion of the) outer surface thereof, in accordance with an exemplary embodiment of the present invention;

FIG. 7D is a schematic diagram illustrating side and front views of an exemplary embodiment of the cannula whose invasive section includes one anchoring element protruding from the (lower portion of the) outer surface thereof, in accordance with an exemplary embodiment of the present invention;

FIGS. 8A-D are schematic diagrams illustrating side views of different exemplary embodiments of the cannula whose invasive section includes one anchoring element protruding from the (upper portion of the) outer surface thereof, wherein each anchoring element features a different exemplary configuration and profile having different exemplary geometric shape and size dimensions (e.g., height [h] above the outer surface, outer radius [R], and ratio [h/R]<1 thereof), in accordance with an exemplary embodiment of the present invention;

FIGS. 9A-C are schematic diagrams illustrating exemplary embodiments of a method for using an exemplary embodiment of the catheter, wherein FIG. 9A shows provision of a catheter including a needle and the exemplary embodiment of the cannula illustrated in FIG. 7B; FIG. 9B shows insertion of the cannula invasive section into a treatment space such that the anchoring elements increase the outer circumferential diameter of the cannula to an extent less than lumen diameter of the body vessel, duct, or cavity, thereby anchoring the invasive section to inside the body vessel, duct, or cavity, at the treatment space; and FIG. 9C shows the catheter cannula after withdrawal of the needle, ready for administering fluid or/and substance to, or draining fluid or/and substance from, the treatment space of the body vessel, duct, or cavity, via the cannula, wherein cannula anchoring elements make no contact with the body vessel wall, in accordance with an exemplary embodiment of the present invention;

DESCRIPTION OF SPECIFIC EMBODIMENTS OF THE INVENTION

Figure 1:
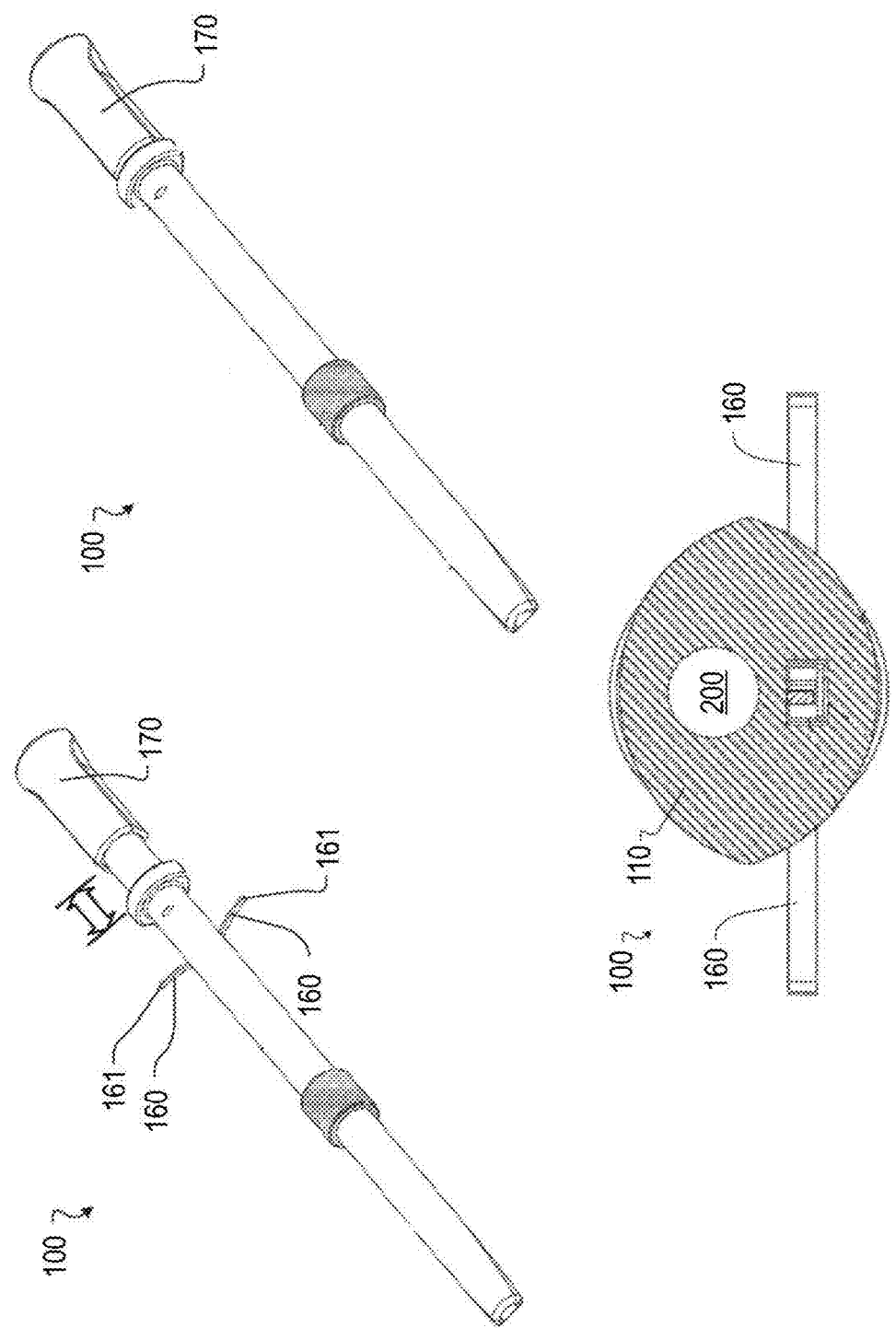
FIG. 1 (prior art) is a schematic diagram illustrating an exemplary prior art catheter apparatus having an anchoring mechanism.
Figure 2:
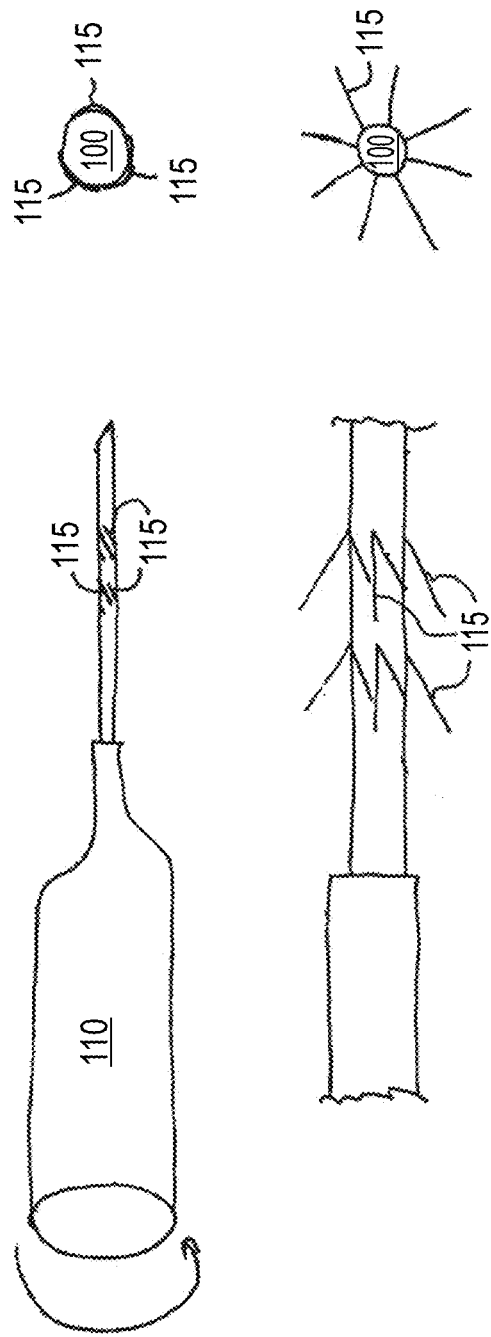
FIG. 2 (prior art) is a schematic diagram illustrating another exemplary prior art catheter apparatus having an anchoring mechanism.
Figure 3:
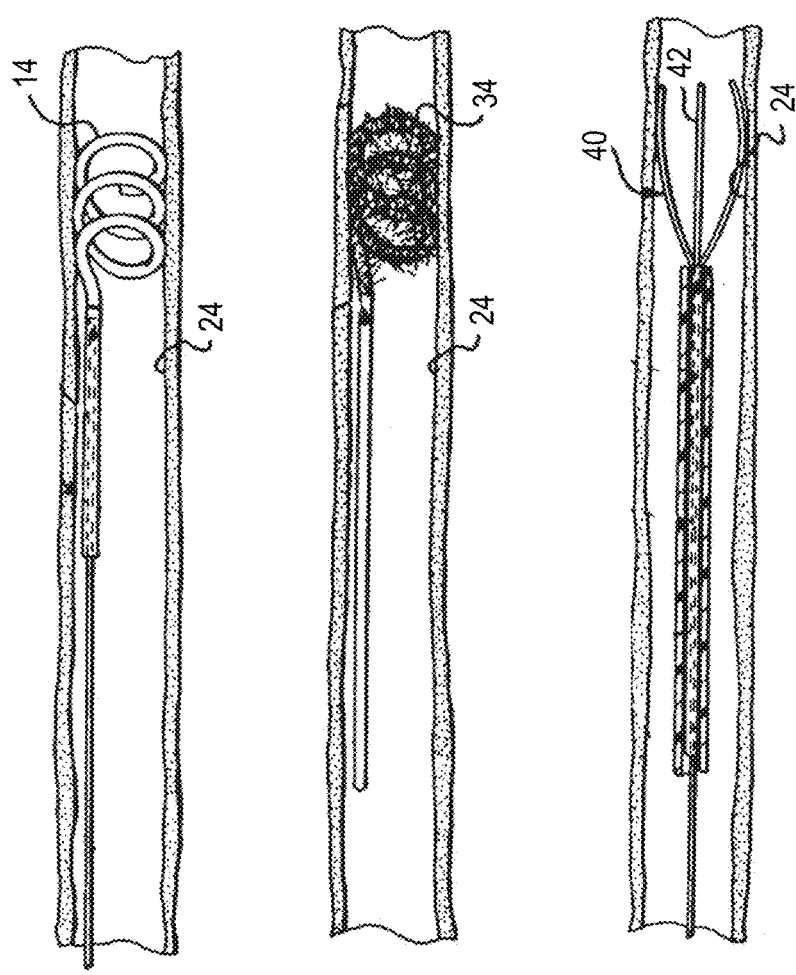
FIG. 3 (prior art) is a schematic diagram illustrating another exemplary prior art catheter apparatus having an anchoring mechanism.
Figure 4:
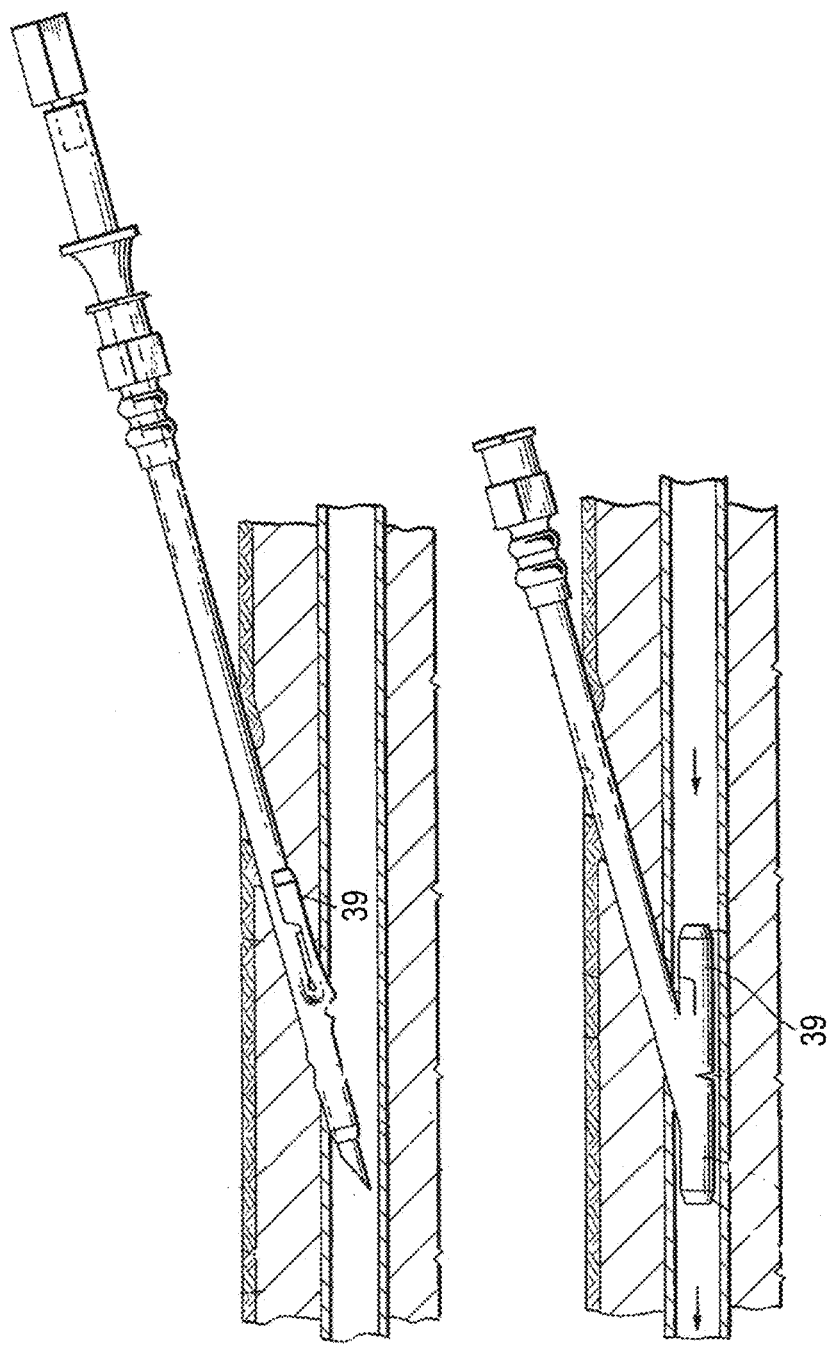
FIG. 4 (prior art) is a schematic diagram illustrating another exemplary prior art catheter apparatus having an anchoring mechanism.
Figure 5:
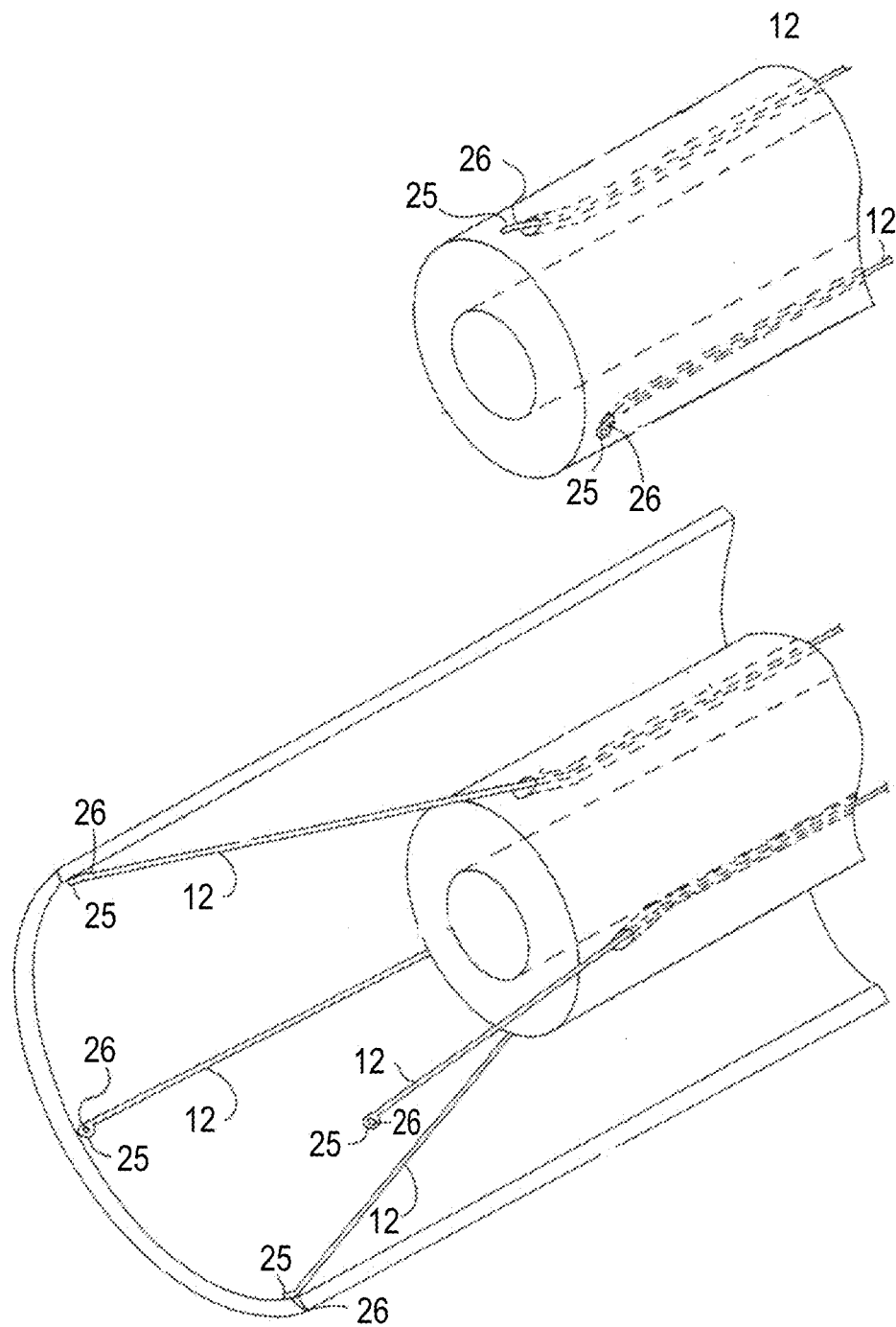
FIG. 5 (prior art) is a schematic diagram illustrating another exemplary prior art catheter apparatus having an anchoring mechanism.

The present invention, in some embodiments thereof, relates to catheter cannulas (cannulas), catheters, and catheterization methods, and, more particularly, but not exclusively, to a cannula, a catheter, and/or a (catheterization) method, for administering a fluid or/and substance to, or for draining a fluid or/and substance from, a treatment space of a body vessel, duct, or cavity. Exemplary fluids or/and substances are drugs, infusion therapy products, and blood products.

An aspect of some embodiments of the invention of the invention relates to a catheter with an anchoring mechanism, in which the mechanism increases the catheter external cross-section so as to reduce likelihood of pull-out, while avoiding or reducing contact with the vessel wall. In an exemplary embodiment of the invention, the reduced contact includes avoiding applying force to two opposing sides of the vessel such that the vessel is distorted by the applied force. Optionally or alternatively, the reduced contact includes not piercing the vessel wall with wall damaging elements.

In an exemplary embodiment of the invention, the anchoring mechanism includes a protrusion on a tube of the catheter which is used for fluid communication between the vessel and the outside of the body. Optionally, the protrusion is fixed. Optionally, such a protrusion is axially asymmetric, in that it has a sloped leading edge to assist in insertion and a more abrupt trailing edge, to assist in preventing removal. While the trailing edge may have an angle of, for example, 60 degrees with respect to the catheter surface, other angles, such as 90 degrees (perpendicular) and 120 degrees (undercut) may be provided. Optionally, the protrusion is at least partially spirally laid along the catheter so that rotation may be used to aid in insertion and/or removable.

In some embodiments of the invention, the protrusion changes shape during before and/or after insertion. Optionally, an overtube is provided to control the shape of the protrusion during insertion. Optionally, there is no extant protrusion during insertion. In an exemplary embodiment of the invention, the shape and/or position of the protrusions are controlled from outside the body, for example, using the overtube, for example, axially sliding and/or rotating the overtube to reveal a protrusion so it can extend radially.

In an exemplary embodiment of the invention, the protrusion provides only a small increase in maximum diameter to the catheter, for example, 20%, 30%, 40%, 50% or smaller, intermediate or larger percentages.

In an exemplary embodiment of the invention, the protrusion is asymmetric with respect to the catheter. Optionally, this asymmetry causes the protrusion to be aligned with a vessel wall, when a catheter is inserted into a vessel (typically at a shallow angle). Optionally, the protrusion is a ring shaped protrusion. Alternatively, the protrusion includes one or more separate protrusions arranged around the catheter, covering, for example, 10%, 20%, 40%, 60%, 80% or smaller or intermediate or greater percentages of its circumferences (when viewed tip on).

In an exemplary embodiment of the invention, a plurality of protrusions are provided axially along the catheter, to support multiple catheter positions in the vessel. For example, successive protrusions may be larger in diameter, so if a first protrusion is not sufficiently diameter-increasing to anchor the catheter, the catheter is pushed in past a next, larger diameter, protrusion. Alternatively a kit having catheters with different protrusions sizes is provided, or a set of catheters, each with different sizes are provided and a physician chooses a catheter according to, for example, need, vein diameter and/or previous failures in anchoring. Optionally, standard anchoring techniques, for example, wings on the part of the catheter that is outside of the body, are provided. In an exemplary embodiment of the invention, the cannula is used with veins of diameter between 1 mm and 5 mm, for example, 3 mm. Larger sizes, as well as arteries of such sizes may be used as well. Optionally, the vein is a surface vein. Alternatively, the vein is a deep vein.

In an exemplary embodiment of the invention, the length of an invasive section of the cannula is, for example, 25 mm, for example, for a 2 mm or 1.7 mm outer diameter cannula (e.g., 14G and 16G, respectively). Similar ratios may be used for other diameter cannulas.

While not meant to be necessarily limiting, the protrusion design may be selected, for example, to resist an inadvertent retraction force of, for example, 0.5 Newton, 1 Newton, 10 Newton, 20 Newton, or smaller or intermediate or greater forces. Optionally, the resistance is selected to reduce damage to the tissue should a large retraction force occur, which matching small forces encountered in typical usage and movements.

An aspect of some embodiments of the invention relates to a method of inserting a catheter into a body, in which after that catheter is inserted, its cross-sectional diameter is enlarged to reduce inadvertent removal. In an exemplary embodiment of the invention, this increase is maintained over long periods of time, for example, a few (1-5) minutes, hours or days, for example, over 80% or more of the usage of the device. In an alternative method, a protrusion is present which increases the diameter also before insertion. In an exemplary embodiment of the invention, the protrusion includes a leading edge designed for insertion and a trailing edge designed to prevent retraction. Insertion includes advancing the catheter into a vessel until the trailing edge is all within the vessel lumen.

A particular feature of some embodiments of the invention is that the anchoring element is mounted on and/or is integral with the same tube used for fluid flow. This means, that for some embodiments of the invention, that the diameter of this tube need not be reduced by providing an anchoring mechanism. In some embodiments, a separate, overtube, is provided to modify the deformation of the fluid flow tube and anchoring element. Such an overtube can be a simple thin tube and need not affect the flow cross-section of the tube substantially (e.g., or require a larger diameter penetration into vessel). In other embodiments, the outer tube is thicker, but the inner tube is made thin, as support and mechanical control is optionally provided by the outer tube. In either case, in some embodiments of the invention it is desirable to reduce the increased thickness of the cannula, so as to maximize a cross-sectional flow for a give cannula outer diameter.

A particular feature of some embodiments of the invention is that contact with the vessel walls are reduced, especially such contact that may cause distortion of the wall. Optionally, some pressure is provided, but only at or near the point of penetration into the vessel and not at other points. A potential benefit of this approach is that veins, which are easily damaged, are less damaged and possibly less prone to inflammation, collapse or other negative side effects of catheterization.

In an exemplary embodiment of the invention, the anchoring of the catheter allows a shorter catheter to be used, which may reduce the length of catheter used in the vessel, again, potentially reducing damage and/or irritation thereof. In an exemplary embodiment of the invention, the invasive section of the cannula that remains in the body is less than 20 times, 18 times, 15 times, or 12 times the outer diameter of the cannula (not including the protrusion)

According to an aspect of some embodiments of the present invention there is provided a cannula for administering a fluid or/and substance to, or for draining a fluid or/and substance from, a treatment space of a body vessel, duct, or cavity, the cannula comprising: an elongated flexible tube mountable on a needle, and having an invasive section and a non-invasive section; and at least one anchoring element (optionally mounted on) protruding from a surface of the invasive section in a manner such that an operative configuration of the at least one anchoring element increases outer circumferential diameter of the cannula to an extent less than lumen diameter of the body vessel, duct, or cavity, at the treatment space, thereby anchoring the invasive section to inside the body vessel, duct, or cavity, at the treatment space, at least against retraction.

According to an aspect of some embodiments of the present invention there is provided a catheter for administering a fluid or/and substance to, or for draining a fluid or/and substance from, a treatment space of a body vessel, duct, or cavity, the catheter comprising: a needle, configured for insertion into the treatment space of the body vessel, duct, or cavity; a cannula, configured as an elongated flexible tube optionally mounted on the needle, the cannula having an invasive section and a non-invasive section, and at least one anchoring element (optionally mounted on) protruding from a surface of the invasive section in a manner such that an operative configuration of the at least one anchoring element increases outer circumferential diameter of the cannula to an extent less than lumen diameter of the body vessel, duct, or cavity, at the treatment space, thereby anchoring the invasive section to inside the body vessel, duct, or cavity, at the treatment space.

According to an aspect of some embodiments of the present invention there is provided a method of administering a fluid or/and substance to, or for draining a fluid or/and substance from, a treatment space of a body vessel, duct, or cavity, the method comprising: inserting a catheter comprising a needle having a cannula optionally mounted thereon into the treatment space of the body vessel, duct, or cavity, wherein the cannula is configured as an elongated flexible tube having an invasive section and a non-invasive section, and having at least one anchoring element (optionally mounted on) protruding from a surface of the invasive section; inserting the invasive section into the treatment space in a manner such that the at least one anchoring element increases outer circumferential diameter of the cannula to an extent less than lumen diameter of the body vessel, duct, or cavity, thereby anchoring the invasive section to inside the body vessel, duct, or cavity, at the treatment space; and administering the fluid or/and substance to, or draining the fluid or/and substance from, the treatment space of the body vessel, duct, or cavity, via the cannula.

In some exemplary embodiments of the invention, the at least one anchoring element protruding from a surface of the invasive section, is designed, constructed, and operates, according to either one of two main types of structural/functional modes or configurations, namely, a 'fixed' type of structural/functional mode or configuration, and a 'movable' type of structural/functional mode or configuration, with respect to the surface of the invasive section of the cannula. For each main type (namely, 'fixed' type or 'movable' type) of structural/functional mode or configuration, the operative configuration (namely, 'fixed' or 'movable' relative to the invasive section of the cannula) of the at least one anchoring element increases the outer circumferential diameter of the cannula to an extent less than the lumen diameter of the body vessel, duct, or cavity, at the treatment space, thereby anchoring the invasive section to inside the body vessel, duct, or cavity, at the treatment space. It is noted, however, that in a shallowly inserted catheter, it is possible for a protrusion to be used (e.g., in a configuration non-perpendicular to the cannula) in accordance with some embodiments of the invention which does cause the cannula to have, at the protrusion a diameter similar or larger than the vessel, without contacting walls on opposite side so the vessel.

In an exemplary embodiment of the 'fixed' type of structural/functional mode or configuration, each anchoring element is 'fixedly' mounted on, and attached at, some point along the wall of the outer surface of the invasive section of the cannula, and remains fixed (in its entirety) with respect to the invasive section of the cannula, (at all stages, except possibly being distorted by surrounding tissue as it is inserted into the body) during use of the cannula in a catheter for administering fluid or/and substance to, or draining fluid or/and substance from, a treatment space of a body vessel, duct, or cavity, via the cannula. Accordingly, for the 'fixed' type of structural/functional mode or configuration, the 'operative configuration' of each anchoring element relative to the invasive section of the cannula) corresponds to each anchoring element (in its entirety) remaining 'fixed' relative to the outer surface of the invasive section of the cannula.

Depending on the embodiment, each anchoring element may be, for example, integral to the invasive section, or non-integral to (separate from, but attached or connected to), the invasive section, of the cannula, where, in each case, the anchoring element is still part (via being mounted on, and protruding from, a surface) of the invasive section of the cannula.

In some embodiments, the protrusion is provided by distorting the wall of the tube of the catheter, for example, during manufacture. In other embodiments, the tube is created in a mold, for example, using extrusion, or using injection molding, using a mold that defines the protrusion and/or using a combination of extrusion and molding. In other embodiment, the protrusion is provided by mounting (e.g., welding or adhesive) of a protrusion on the catheter.

In some exemplary embodiments of the 'movable' type of structural/functional mode or configuration, each anchoring element is 'movably' mounted on, and attached at, some point along the wall of the inner surface invasive section of the cannula or formed of the wall itself or is an axial extension thereof, and is moved with respect to the invasive section of the cannula, (e.g., at an initial stage, and at a final stage) during use of the cannula in a catheter for administering fluid or/and substance to, or draining fluid or/and substance from, a treatment space of a body vessel, duct, or cavity, via the cannula. Accordingly, for some embodiments of the 'movable' type of structural/functional mode or configuration, the 'operative configuration' of each anchoring element relative to the invasive section of the cannula) corresponds to each anchoring element being 'moved' relative to the inner surface of the invasive section of the cannula, for example, by radially extending.

Depending on the embodiment, each anchoring element may be, for example, integral to the invasive section, or non-integral to (separate from, but attached or connected to), the invasive section, of the cannula, where, in each case, the anchoring element is still part (via being mounted on, and protruding from, a surface) of the invasive section of the cannula.

In some exemplary embodiments of the 'movably' configured anchoring element, each anchoring element is characterized by including two sections, namely, an 'internal' base section, and an 'external' bendable section, with respect to the inner wall of the invasive section of the cannula.

In an exemplary embodiment of the invention, the 'internal' base section of each anchoring element is substantially located and positioned 'internal' along the inner surface of the invasive section of the cannula. The 'internal' base section of each anchoring element is advanced (e.g., pushed in the direction towards the tip of the cannula and into a treatment space) along the inner surface of the invasive section of the cannula, at an initial stage prior to, and optionally retracted at a final stage following, the actual fluid or/and substance administration or delivery. Optionally, the anchoring element substantially remains 'internal' along the inner surface of the invasive section of the cannula, during use of the cannula in a catheter for administering fluid or/and substance to, or draining fluid or/and substance from, a treatment space of a body vessel, duct, or cavity, via the cannula.

In an exemplary embodiment of the invention, the 'external' bendable section of each anchoring element is, for example, typically, at least partly located and positioned 'external' from (outside of, and forward from) the inner surface of the invasive section of the cannula. In general, however, the 'external' bendable section of each anchoring element may be substantially, or even entirely, located and positioned internal along the inner surface of the invasive section of the cannula. The 'external' bendable section of each anchoring element is moved (pushed) further outside of, and forward from, the inner surface of the invasive section of the cannula, at an initial stage prior to, the actual fluid or/and substance administration or delivery, and remains 'external' from (outside of, and forward from) the inner surface of the invasive section of the cannula, during use of the cannula in a catheter for administering fluid or/and substance to, or draining fluid or/and substance from, a treatment space of a body vessel, duct, or cavity, via the cannula. Optionally, the external section is retracted relatively to an overtube section of the cannula after fluid flow and prior to removal of the body, so that it radially collapses.

In exemplary embodiments of the 'movably' configured anchoring element, the two main sections, namely, the 'internal' base section, and the 'external' bendable section, of each anchoring element, are configured as a single cylindrical or tubular structure, such as a tube, or tube-like structure, which may be configured, for example, as a 'secondary' internal cannula, that is mountable along the inner surface of the invasive section of the (overall or primary) cannula.

In an exemplary embodiment of the invention, the anchoring element comprises one or more elements which are an extension of the fluid carrying tube and which distort away from said tube when an overtube is retracted. Optionally, the anchoring element does not move axially relative to the cannula flow conduit.

In an exemplary embodiment of the invention, the invasive section of the cannula which goes through and resides within the vessel is designed and constructed to be sufficiently short (e.g., less than 15 times its diameter) so as to minimize any contact between the cannula's invasive section and the vessel wall opposite to the entry point. Subsequently, the cannula is anchored to the vessel's wall at the entry point by using one or more anchoring elements designed to prevent an undesired dislodgement of the cannula, via providing resistance to movement of the cannula from the body vessel, duct, or cavity wall, during a procedure of administering a fluid or/and substance to, or for draining a fluid or/and substance from, a treatment space of a body vessel, duct, or cavity, by mechanical interference with the hole in the vein through which the catheter is inserted. After the invasive section of the cannula is positioned within the treatment space of the body vessel, duct, or cavity vessel and is anchored inside the vessel lumen thereof, the process of administering or draining a fluid or/and substance fluid at the treatment space can take place while minimizing, if not altogether eliminating, the undesired eventuality of cannula dislodgement.

In an exemplary embodiment of the invention, the catheter, including the cannula, is a short peripheral infusion catheter. A short peripheral catheter (SPC) is one of the definitions found in the literature for small infusion catheters that are inserted into peripheral veins. These catheters are usually a few centimeters long, generally, about 5 cm long, depending on their diameter. In some embodiments of the invention, the cannula of the catheter is shorter in the invasive section that is inserted and dwells inside the body vessel, duct, or cavity vessel, so as to minimize any contact with the opposite wall thereof. Optionally, the catheter includes a needle designed for insertion into a designated treatment space of a body vessel, duct, or cavity vessel, and a cannula having an anchoring mechanism, for example as described herein. The cannula concentrically surrounds the inner or outer surfaces of the needle like a sleeve. The cannula is essentially an elongated flexible tube that is inserted into an intravascular treatment area for the delivery or removal of fluids or/and substances.

Placing a catheter in a patient's blood vessel whether it be for a short period of time (a few days) or long periods of time (more than a week), may result in various complications. One such complication is known as thrombophlebitis, which is a sterile inflammation process of the vein wall that may involve thrombosis of the vein lumen. Thrombophlebitis appears on average after 3 days of catheterization, with prevalence that ranges widely from 3% to 80% of the hospitalized patients. Putting aside the inconvenience caused by thrombophlebitis to patients, it may also complicate further medical care required, and consequently prolong hospitalization and accompanied financial costs.

The pathogenesis of catheter-related thrombophlebitis still remains not well understood; however, it can be argued that this phenomenon is caused by contact between the cannula inserted into the vein lumen and the vein's wall. Specifically, the contact between the cannula and the endothelial cells which cover the vein's wall cause these cells to secrete inflammatory substances which are key contributors to thrombophlebitis formation. Another potentially important issue with respect to catheter usage on patients is their susceptibility for movement. Namely, any movement made by a patient while the catheter is placed within a vessel may result in an accidental dislodgement of the catheter from the vein and/or wall irritation.

Optionally, the cannula disclosed herein is significantly shorter in its invasive section, the section that goes through an intravascular treatment space and resides within it. Making the length of the cannula's invasive section shorter in size, can reduce contact with the vessel's wall opposite to the insertion point of the cannula into the intravascular treatment area, or at the very least minimizes the chance of a possible contact between the cannula and the vessel's wall.

As outlined herein, in an exemplary embodiment of the invention, the cannula includes an anchoring mechanism designed to prevent a possible dislodgment of the cannula from the intravascular treatment area while the process of administering fluids is taking place. Optionally, the anchoring elements are one or more protrusion/bumps which are mounted and attached to the cannula, for example onto its outer surface, in close proximity to its invasive section. In use, the anchoring elements anchor the cannula to the vessel inner wall, thus preventing an accidental dislodgement of the cannula from the intravascular treatment area due to the patient's movements for instance. The anchoring elements may be protrusions which geometrically vary in size so long as the protrusion's height is less than the outer diameter of the cannula. In case a number of protrusions are used, the same rule may apply to each one of them.

Optionally, the cannula and/or the protrusions are made of a single polymer/material. Optionally, the protrusions have a lower rigidity coefficient than the cannula's material, for example made of a softer material and/or structure. When the anchoring elements are made from the same polymer/material as the cannula's material, for example using a single mold, the manufacturing costs can be substantially similar to the manufacturing costs of the cannula itself. In addition, the manipulation and use of the product remains almost similar to other known products and therefore does not require any substantial training.

Another potential advantage that arises from the above mentioned structure is that the resistance of the lumen of the cannula to flow reduces. Namely, that high flow rates may be achieved, or alternatively, smaller diameter catheters may be used for the same required flow rates. This is made possible due to the shorter length of the cannula.

It should be noted that the devices and methods described herein do not necessarily impose limitations with respect to additional features which may be added externally such as wings that support with ease the outer fixture of the cannula and catheter to the skin, or any other known commercial products which may be externally added onto the cannula or catheter apparatus.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 6:
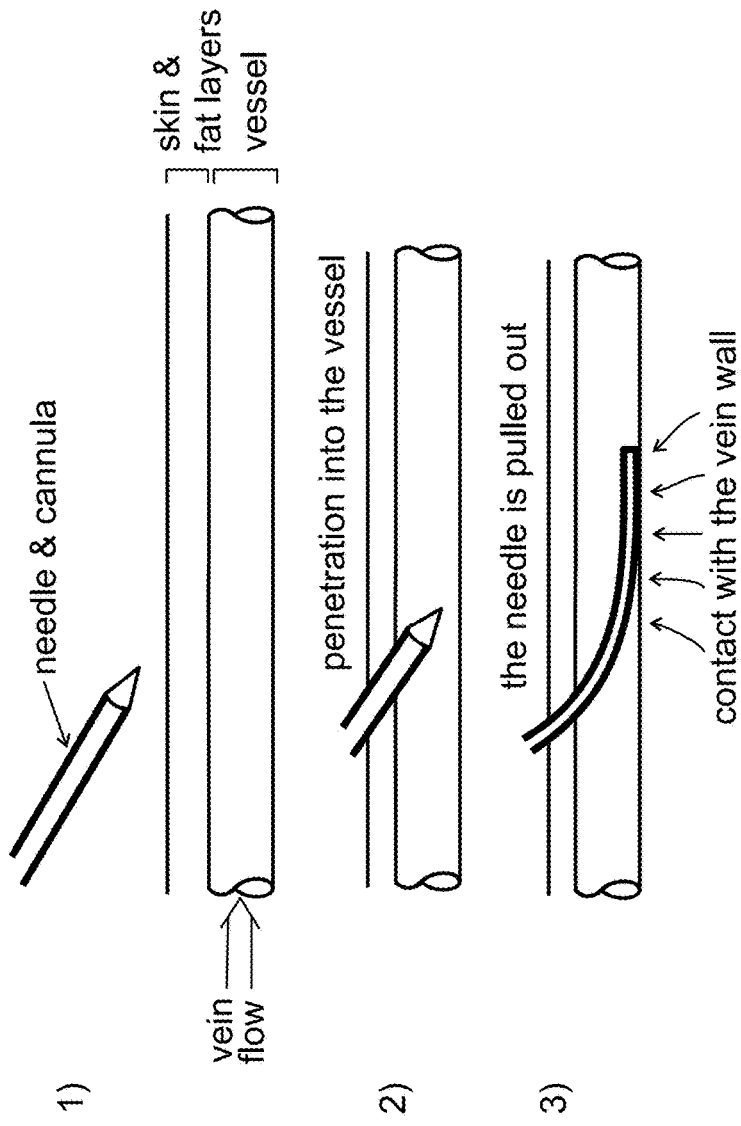
FIG. 6 (prior art) is a schematic diagram illustrating the mechanism of commercially available short peripheral infusion catheters, wherein contact of the catheter polymeric body and the vessel (vein) wall is almost inevitable due to the entrance angle of the catheter into the vessel.

The mechanism or mode of operation of commercially available short peripheral infusion catheters inevitably involves contact of the catheter body with an opposite vessel (e.g., vein) wall, due to the entrance angle of the catheter into the vessel, for example, as shown in FIG. 6. Contact between the catheter body with the vessel wall, especially during prolonged (chronic) placement of the catheter in a patient's blood vessel, often results in catheter failure (via catheter occlusion or local inflammation in the vessel wall). This may be caused, for example, due to aspiration of the blood vessel wall into the tip of the catheter, clot or thrombus formation at the tip of the catheter, stenosis around the tip of the catheter, inflammation (e.g., phlebitis) and/or damage to the vessel walls. Currently, catheter occlusions caused by aspiration of the blood vessel wall or clot formation at the catheter tip may be resolved by repositioning the catheter tip or infusing antithrombotic agents. When local inflammation (phlebitis) occurs, the solution is typically to remove the catheter and to insert a new one into another vein, or same vein other site.

In an exemplary embodiment of the invention, a catheter is provided which reduces the inflammatory process initiated due to the catheter presence. Some embodiments of the invention reduce contact of the cannula with the wall and/or reduce or prevent damaging forces.

The herein disclosed cannula, in some exemplary embodiments thereof, is applicable, but not limited, for being a main component of some exemplary embodiments of the herein disclosed catheter, for administering a fluid or/and substance to, or for draining a fluid or/and substance from, a treatment space of a body vessel, duct, or cavity. Moreover, the herein disclosed catheter, in some exemplary embodiments thereof, is applicable, but not limited, for performing some exemplary embodiments of the herein disclosed method of administering a fluid or/and substance to, or for draining a fluid or/and substance from, a treatment space of a body vessel, duct, or cavity.

Some embodiments of the invention enable maintenance of vascular access for short periods of time (a few days). The catheter is a short peripheral infusion catheter and includes two main components: a needle, such as a stainless steel needle, and a cannula, for example, constructed of polymeric material such as derivations of polyurethane or Teflon. The needle may be used for providing easy penetration into a treatment space of a body vessel, duct, or cavity (e.g., vessel (vein, artery) lumen). After intravascular access is achieved by the needle, the needle is pulled out and the cannula remains partially inside the treatment space, desirably only a short distance, thus enabling prolonged intravascular access. In an exemplary embodiment of the invention, such prolonged access is provided without indwelling sharp objects. FIG. 6 shows, in contrast, a standard method of implanting a catheter, showing that contact with the far wall, and potential associated irritation is inherent in the standard method.

Some embodiments of the invention use an indwelling anchoring element so a shorter indwelling section may be used. According to some embodiments of the invention, the cannula includes an invasive section (e.g., that part of the cannula which is intended to and designed for becoming invasive to the treatment space of the body vessel, duct, or cavity) which is optionally significantly shorter in length than the invasive section of commercially available products, so that contact between the invasive section of the cannula with the opposite wall of the body vessel, duct, or cavity, will be eliminated, or at least will be significantly reduced, for example, by 80%, 50%, 30% or intermediate amounts. Optionally, the section of wall that is in contact with the cannula is of length of less than 5 cm, less than 3 cm, less than 2 cm, less than 1 cm, or even less than 0.5 cm.

Implementation of some embodiments of the present invention can be used to enable hospitalized patients to achieve quick administration of drugs, infusion therapy, blood products, etc., without repeatedly puncturing blood vessels of patients.

FIG. 7A is a schematic diagram illustrating side and front views of an exemplary embodiment of the cannula 10 whose invasive section 12 includes two anchoring elements 14 and 16 (optionally, each featuring a 'fixed' type structural/functional mode or configuration) protruding from, the outer surface 18 of the invasive section 12, wherein the anchoring elements 14 and 16 are, for example, diametrically (180°) oppositely positioned relative to each other on upper and lower portions of the outer surface 18 of the invasive section 12.

FIG. 7B is a schematic diagram illustrating side and front views of an exemplary embodiment of the cannula 10 whose invasive section 12 includes two anchoring elements 14 and 16 protruding from the outer surface 18 of the invasive section 12, wherein the anchoring elements 14 and 16 are, for example, diagonally (180°) oppositely positioned relative to each other on upper and lower portions of the outer surface 18 of the invasive section 12. In an exemplary embodiment of the invention, the angle α between the line 13 connecting the protrusions and the axis 15 of the cannula is selected to match the expected insertion angle of the cannula into the vessel. In an exemplary embodiment of the invention, the non-invasive part 12*a* of the cannula is marked (e.g., with a color mark and/or a geometrical shape) so that a physician or technician can use a correct orientation for insertion.

FIG. 7C is a schematic diagram illustrating side and front views of an exemplary embodiment of the cannula 10 whose invasive section 12 includes one anchoring element 14 protruding from, the (upper portion of the) outer surface 18 of the invasive section 12.

FIG. 7D is a schematic diagram illustrating side and front views of an exemplary embodiment of the cannula 10 whose invasive section 12 includes one anchoring element 16 mounted on, and protruding from, the (lower portion of the) outer surface 18 of the invasive section 12.

As can be seen (see also FIG. 11), each protrusion optionally has both a leading edge 37 and a trailing edge 39. Optionally, the leading edge is shaped to be suitable for insertion into a blood vessel through a hole therein. For example, the protrusion may narrow as it nears the leading tip 16a. Optionally or alternatively, the trailing edge is adapted for prevention of retraction, for example, having a greater slope and/or being as wide or wider at its tip as the widest part of the leading section. Optionally, the angle on/or other geometry of the trailing edge is matched to the expected angle of that edge with the vessel wall. Optionally, the trailing edge is designed to have an angle within less than 90 degrees or 45 degrees of the contact angle of the trailing edge with the vessel wall.

FIGS. 8A-D are schematic diagrams illustrating side views of different exemplary embodiments of the cannula 20 whose invasive section 22 includes one anchoring element 24 protruding from the (upper portion of the) outer surface 26 of the invasive section 22, wherein each anchoring element 24 features a different exemplary configuration and profile having different exemplary geometric shape and size dimensions (e.g., height [h] above the outer surface 26, outer radius [R], and/or ratio [h/R] of the height [h] and the outer radius [R]. In exemplary embodiments, the ratio [h/R] of the height [h] and the outer radius [R] is less than one, i.e., [h/R]<1, less than 0.5 or even less than 0.33. The slope of the leading edge may be, for example, uniform or increasing or decreasing towards the peak of the protrusion, depending, for example, on the expected resistance of tissue to insertion. In the trailing slope, the slope is optionally determined by the functional form of the resistance force to retraction.

In exemplary embodiments, the ratio between the cannula's outer circumferential diameter [D] (for example, as shown in FIGS. 7A-D), and the length [L] of the invasive section 22 of the cannula 20, is no less than 0.06 or 0.2.

In an exemplary embodiment of the invention, the protrusion has a length of between 4 times and 1 time the cannula external diameter, for example, twice the diameter. Optionally, the leading edge of the protrusion is longer than the trailing edge, for example, by a factor of 1.1, 2, 3 or intermediate values.

For example, the cannula's outer circumferential diameter [D] is about 2 mm (e.g., about a 14 gauge catheter) and the invasive section 22 which is set to penetrate the vein has a length [L] of about 24 mm (or shorter, for example, 10 mm or 7 mm). In exemplary embodiments of the cannula including two anchoring elements (e.g., circumferentially arranged and/or axially arranged with respect to each other, each anchoring element may feature a different exemplary configuration and profile having different exemplary geometric shape and size dimensions (e.g., height [h] above the outer surface, outer radius [R], and/or ratio [h/R] of the height [h] and the outer radius [R]). In an exemplary embodiment of the invention, h/R is between 2 or 1 and 0.1, for example, between 1.1 and 0.3, for example, less than 0.5. In an exemplary embodiment of the invention, the length of the protrusion (leading tip to trailing tip) is between 15 mm and 1 mm, for example, between 2 mm and 10 mm, for example, less than 8 mm. In an exemplary embodiment of the invention, the leading edge is at least 110%, 150%, 200%, 300% or smaller or intermediate or greater percentages of the trailing edge length.

FIG. 8A shows a trailing edge with a slope that is greater than that of the leading edge. For example, the slope can be a factor of 1, 2, 3, 4, or intermediate or greater factors of the slope of the leading edge.

FIG. 8B shows a steeper trailing edge slope.

FIG. 8C shows a more gradual trailing slope, also showing that the slope can be rounded rather than linear.

FIG. 8D shows a protrusion with linear slopes. Exemplary slope angles for a leading edge are, for example, 5, 10, 20, 30, 40 or intermediate degrees.

In some exemplary embodiments of the cannula, for example, cannula 10 (FIGS. 7A-D), or cannula 20 (FIGS. 8A-D), the anchoring elements (protrusions) are added on or formed with the cannula outer surface in proximity to the cannula tip in order to anchor the cannula slightly inside the vein lumen, thus preventing the short cannula from accidently being pulled outside the vein.

In an exemplary embodiment of the invention, a plurality of axially spaced apart protrusions are provided. Optionally, the vessel wall and skin are intended to be trapped between two such protrusions, preventing inadvertent over-insertion. The protrusions intended to be outside the body and/or vein may be arranged in an opposite direction, with a leading edge having a greater slope then their trailing edges, optionally mirroring the arrangement in the invasive section. Optionally or alternatively, one or more small protrusions are provided in a location where surrounding tissue is expected, so as to assist in anchoring by engaging non-vascular tissue.

However, anchoring to prevent only retraction is sufficient for some embodiments of the invention.

Generally, the cannula's noninvasive section bears no restrictions with respect to any additional features which may be added to the external surface of the cannula. For example, wings that support with ease the outer fixture of the cannula to the skin may be added onto the external surface of the non-invasive section of the cannula.

FIGS. 9A-C are schematic diagrams illustrating exemplary embodiments of a method for using an exemplary embodiment of the catheter, for administering a fluid or/and substance to, or for draining a fluid or/and substance from, a treatment space of a body vessel, duct, or cavity.

FIG. 9A shows provision of a catheter 28 including a needle 34 and the exemplary embodiment of the cannula 10 illustrated in FIG. 7B. Cannula 10 has an invasive section 12 including two anchoring elements, indicated in FIG. 9A as 'upper protrusion' 14 and 'lower protrusion' 16 protruding from the outer surface of the invasive section 12, wherein the anchoring elements 14 and 16 are, for example, diagonally) (180°) oppositely positioned relative to each other on upper and lower portions of the outer surface of the invasive section 12.

FIG. 9B shows insertion of the cannula invasive section 12 into a treatment space, indicated by reference symbol TS, such that the anchoring elements 14 and 16 increase the outer circumferential diameter [D] of the cannula 10 to an extent less than lumen diameter [d] of the body vessel, duct, or cavity, 32 thereby anchoring the invasive section 12 of the cannula 10 to inside the body vessel, duct, or cavity, 32 at the treatment space TS.

FIG. 9C shows the catheter cannula 10 after withdrawal of the needle 34, ready for administering fluid or/and substance to, or draining fluid or/and substance from, the treatment space TS of the body vessel, duct, or cavity, 32 via the cannula 10, wherein the cannula anchoring elements 14 and 16 make no contact with the opposing inner wall of the body vessel 32. It is noted that some vessels, such as veins do tend to collapse and thus may touch the edge of the cannula, but, optionally, no force is being applied by the cannula to cause such contact.

In some embodiments of the invention using anchoring, the cannula is short enough so that it can be stiffer or even rigid while still avoiding forceful contact with the opposing wall. Optionally, such a cannula is inserted without a needle, serving as its own penetration head.

In some embodiments the designs described herein are used for percutaneous or other penetration of tissue, possibly so the cannula anchors in the tissue rather than in a lumen. Optionally, the protrusions are made stiffer for such application. Optionally or alternatively, the leading end of the cannula is sharpened for self penetration. Optionally or alternatively, the cannula itself is made rigid in such an application.

As noted above, in contrast to regular short peripheral infusion catheters, embodiments of the cannula, and catheter including thereof, are aimed, in some embodiments of the invention, to significantly reduce, even eliminate, contact between the cannula and the vessel (e.g., vein) wall. Reduction of this contact should significantly reduce irritation to the vessel wall and therefore may significantly delay thrombophlebitis formation. In an exemplary embodiment of the invention, the length of cannula inside the vessel is, for example, 3 cm, 2 cm, 1 cm, 0.5 cm or smaller or intermediate lengths.

Figure 10A:
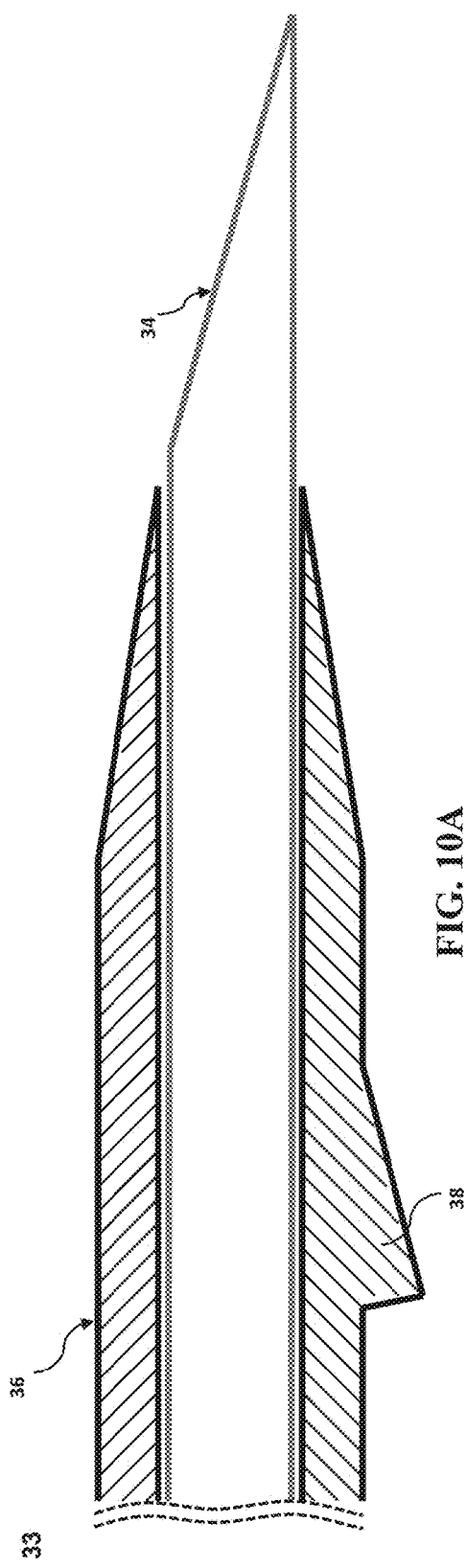
FIG. 10A is a schematic diagram illustrating a cross-sectional side view of an exemplary embodiment of the catheter, including a needle, and a cannula (e.g., as shown in FIG. 7D) whose invasive section includes one anchoring element protruding from the (lower portion of the) outer surface thereof, in accordance with an exemplary embodiment of the present invention.

FIG. 10A is a schematic diagram illustrating a cross-sectional side view of an exemplary embodiment of the catheter 33, including a needle 34, and a cannula 36 (e.g., as shown in FIG. 7D) whose invasive section includes only one anchoring element 38 protruding from, the (lower portion of the) outer surface of the invasive section of the cannula 33.

Figure 10B:
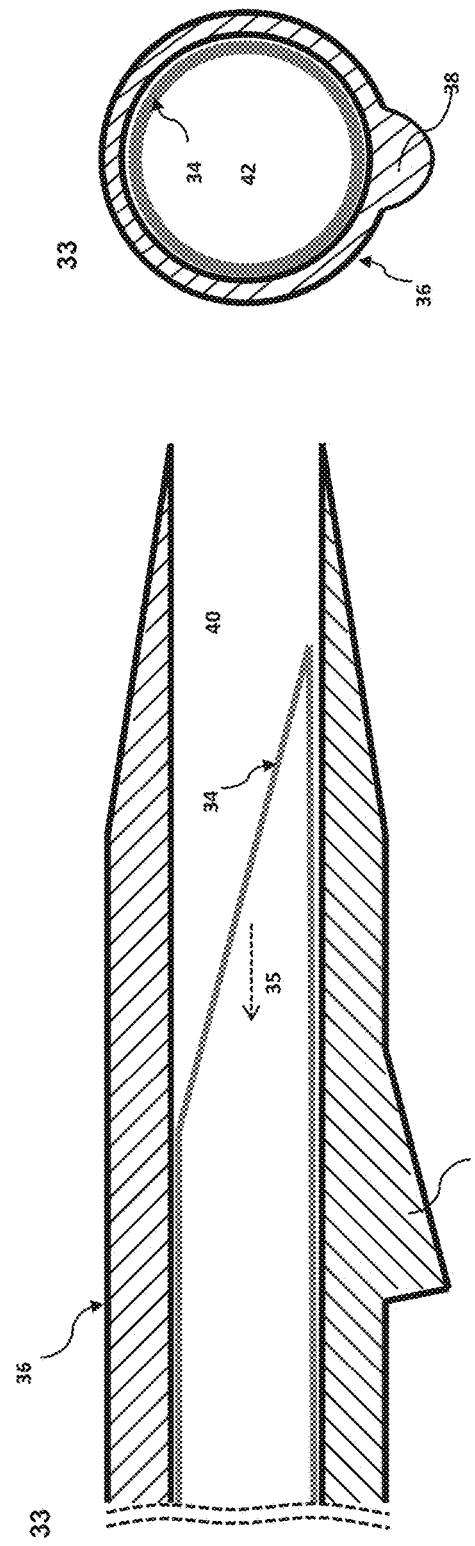
FIG. 10B is a schematic diagram illustrating the same cross-sectional side view shown in FIG. 10A, wherein the needle is being removed from the invasive section of the cannula, in accordance with an exemplary embodiment of the present invention.

FIG. 10B is a schematic diagram illustrating the same cross-sectional side view shown in FIG. 10A, wherein the needle 34 is being removed (indicated by the left-directed arrow with reference number 35), through cannula lumen 40, from the invasive section of the cannula 33. As can be seen in this example, the protrusion has a limited circumferential range.

Figure 10C:
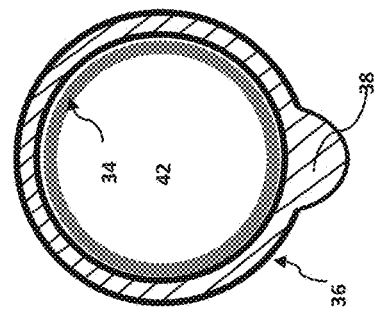
FIG. 10C is a schematic diagram illustrating a cross-sectional front view of the catheter shown in FIGS. 10A and 10B, in accordance with an exemplary embodiment of the present invention.

FIG. 10C is a schematic diagram illustrating a cross-sectional front view of the catheter shown in FIGS. 10A and 10B, also showing the needle lumen 42.

Figure 11:
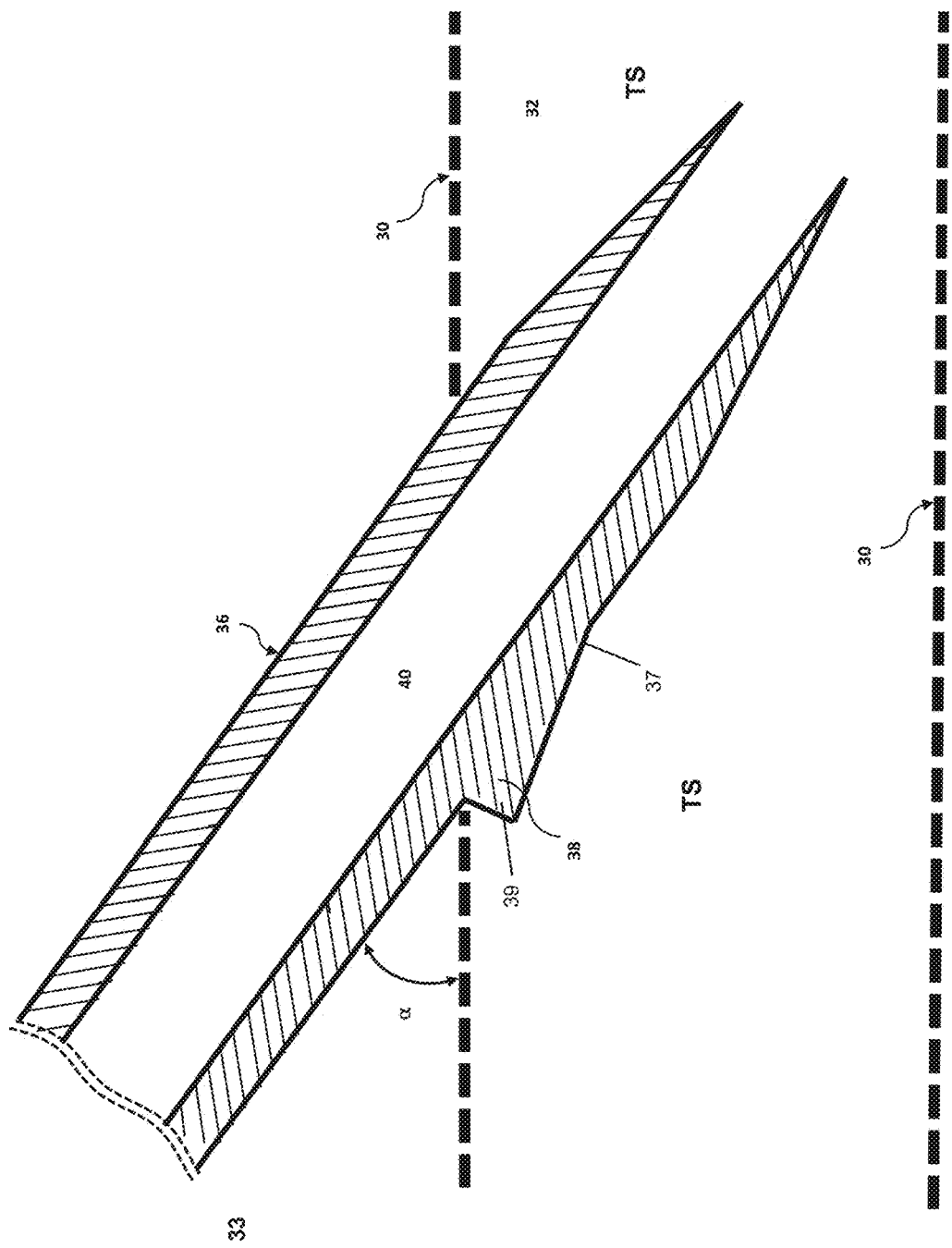
FIG. 11 is a schematic diagram illustrating a cross-sectional side view of the catheter shown in FIGS. 10A, 10B, and 10C, wherein the needle has been removed, and the invasive section of the cannula is inserted into a treatment space of a body vessel, duct, or cavity, particularly highlighting operative location, position, and configuration of the anchoring element within the treatment space, and highlighting the angle (α) [e.g., 10-45°] in which the invasive section of the cannula is inserted into the treatment space, in accordance with an exemplary embodiment of the present invention.

FIG. 11 is a schematic diagram illustrating a cross-sectional side view of the catheter 33 shown in FIGS. 10A, 10B, and 10C, wherein the needle 34 has been removed from the cannula lumen 40, and the invasive section of the cannula 36 is inserted into a treatment space TS of a lumen 32 of a body vessel, duct, or cavity, particularly highlighting operative location, position, and configuration of the anchoring element 38 (contacting, and anchoring the invasive section to, the vessel, duct, or cavity, wall 30) within the treatment space TS, and highlighting the angle (α) [e.g., 10-45°] in which the invasive section of the cannula 36 is inserted into the treatment space TS. In exemplary embodiments, the angle (α) in which the invasive section of the cannula 36 is inserted into the treatment space TS has a value in a range of between about 5° and about 75°, for example, between 10° and 45° or 35°, in accordance with known procedures for inserting an invasive section of a cannula of a catheter into a treatment space of a body vessel, duct, or cavity.

Figure 12:
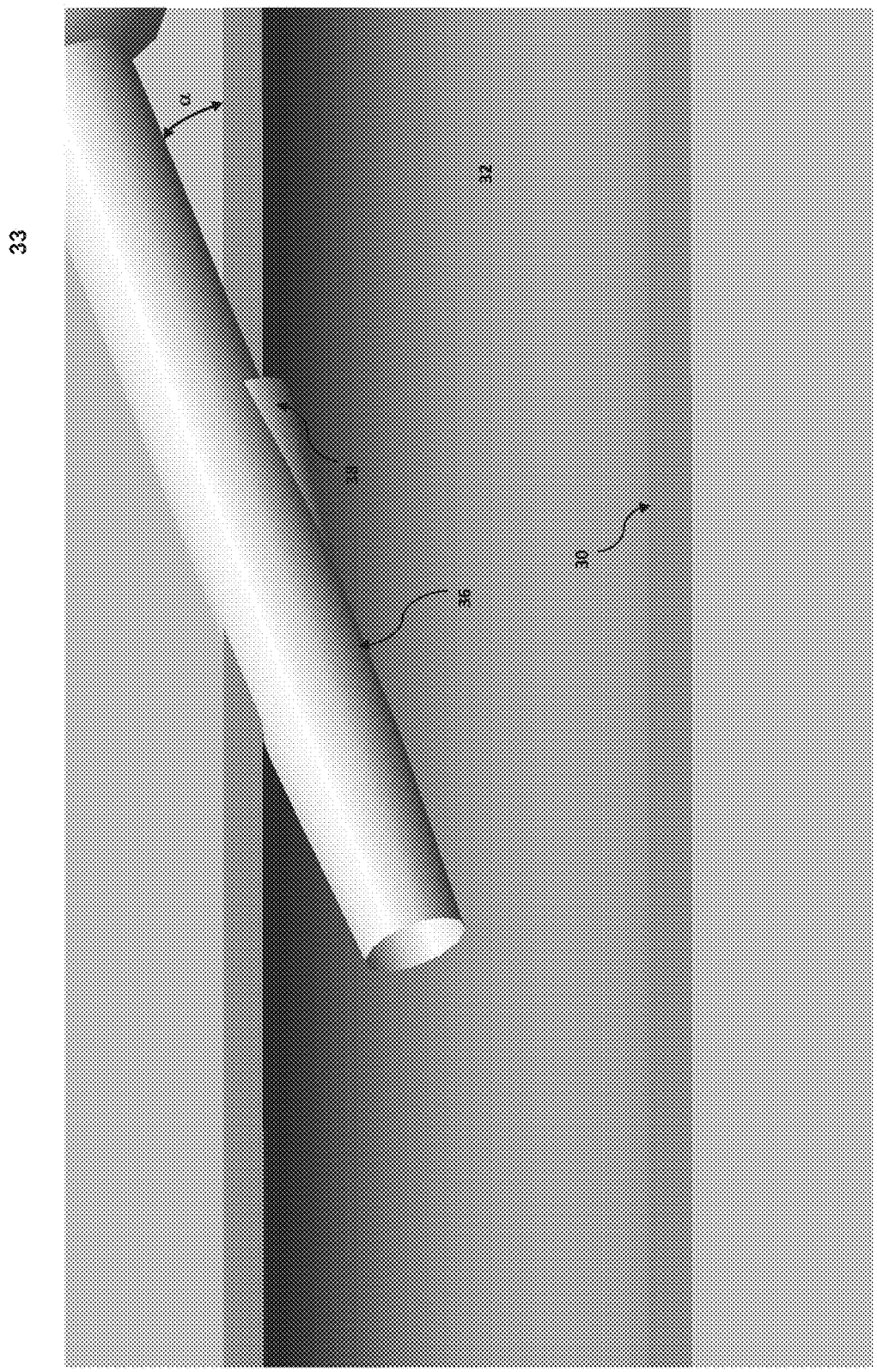
FIG. 12 is a pictorial diagram illustrating a perspective view of the catheter shown in FIGS. 10A, 10B, 10C, and 11, wherein the needle has been removed, and the invasive section of the cannula is inserted into a treatment space of a body vessel, duct, or cavity, particularly highlighting exemplary operative location, position, and configuration of the anchoring element within the treatment space, and highlighting the angle (α) [e.g., 10-45°] in which the invasive section of the cannula is inserted into the treatment space, in accordance with an exemplary embodiment of the present invention.

FIG. 12 is a pictorial diagram illustrating a perspective view of the catheter 33 (including a 'fixed' type anchoring element 38) shown in FIGS. 10A, 10B, 10C, and 11, wherein the needle 34 has been removed, and the invasive section of the cannula 36 is inserted into a treatment space TS within a lumen 32 of a body vessel, duct, or cavity. The exemplary embodiment illustrated in FIG. 12 particularly highlights operative location, position, and configuration of the anchoring element (contacting, and anchoring the invasive section to, a vessel, duct, or cavity, wall 30) within the treatment space TS, and highlighting the angle (α) [e.g., 10-45°] in which the invasive section of the cannula 36 is inserted into the treatment space TS.

Figure 13:
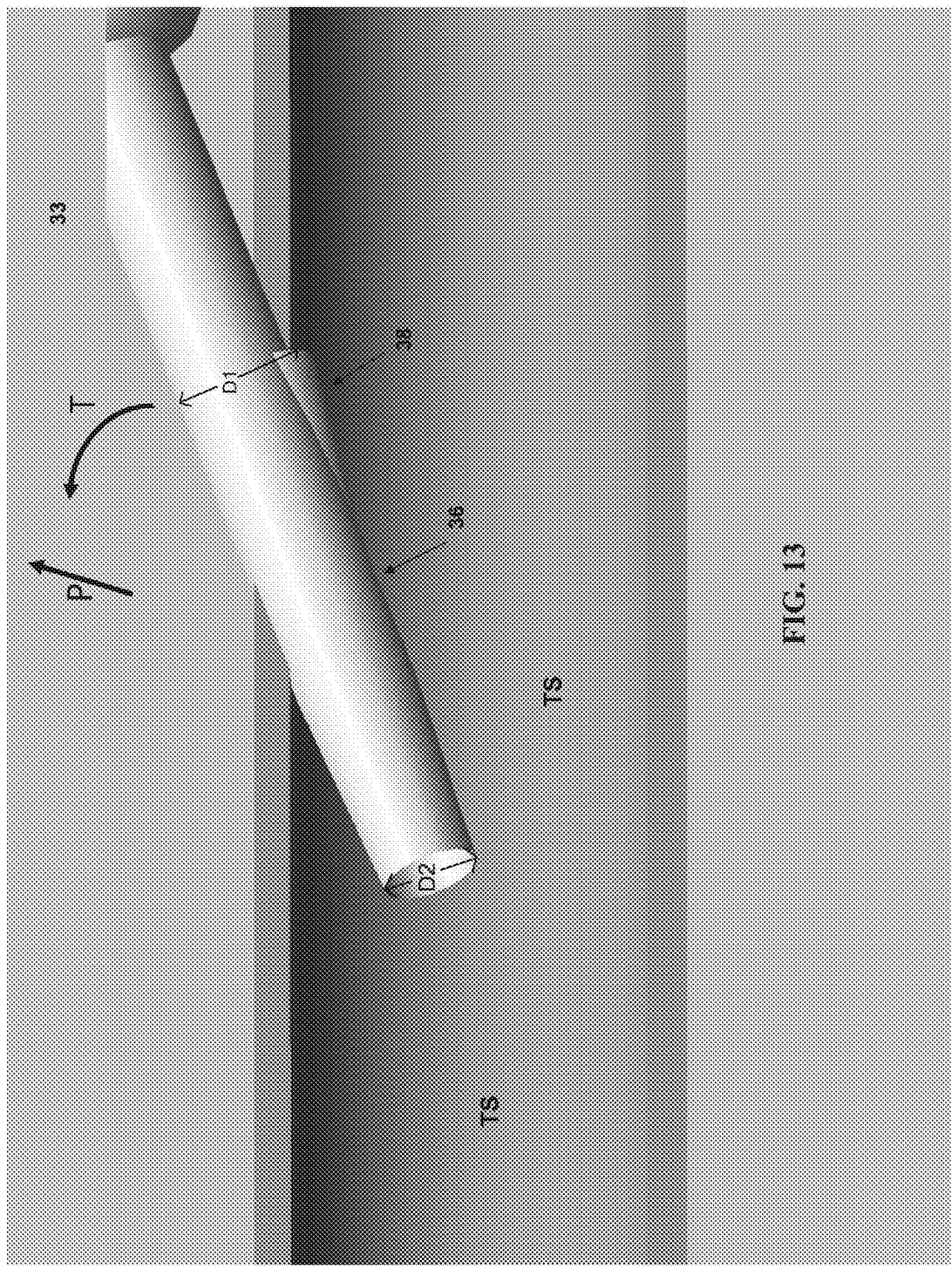
FIG. 13 is a pictorial diagram illustrating the same perspective view of the inserted catheter shown in FIG. 12, particularly, highlighting a twisting (T) motion and a pulling (P) motion, which may be used for removing (e.g., via twisting or rotating and pulling) the invasive section of the cannula out from the treatment space of the body vessel, duct, or cavity, in accordance with an exemplary embodiment of the present invention.

FIG. 13 is a pictorial diagram illustrating the same perspective view of the inserted catheter 33 (including the 'fixed' type anchoring element 38) shown in FIG. 12, particularly highlighting a twisting (T) motion and a pulling (P) motion, which may be used for removing (via turning the cannula in the plane of the figure and pulling) the invasive section, including the anchoring element 38, of the cannula 36 out from the treatment space TS of the body vessel, duct, or cavity. In an exemplary embodiment of the invention, such turning reduces the effective diameter D1 of the cannula and protrusion peak with respect to the aperture in the vessel, from D1 to a smaller effective diameter D2, so it can be more easily removed. Optionally or alternatively, the rotating is used to align the slope of the trailing edge of the protrusion with the aperture, so the sloping is more gradual when retracting the cannula. Optionally or alternatively, the cannula may be twisted so as to realign the protrusion with respect to the aperture. For example, a protrusion which is more resistant at the bottom of a cannula, may be less resisting to removal when rotated to an "upper" position, or vice versa. Optionally or alternatively, twisting is used to assist in the removal by assisting in sliding. Optionally, the protrusion or trailing edge thereof includes a helical arranged portion (optionally less than a full turn, but possibly more), such that twisting can be used to screw the catheter out of the vessel.

It should be noted that while the protrusions have been generally shown as solid elements, this is not the case in all embodiments. In one example, a protrusion is formed as a hollow element 19 (FIG. 9B), for example, including a cavity or formed by heat-working or by mold-injection or by extrusion of the cannula tube or by combined molding and extrusion. This means that the thickness of the cannula material at the protrusion may be the same or even less than at other parts of the cannula. One possible advantage is that such a cannula can be inserted into the body through an over tube (optionally a tear-away overtube) which maintains the protrusion in a collapsed condition until it is released by axially retracting the over tube. In another example, an overtube has a window matching a protrusion, so that when rotated so that the window overlies the protrusion, the protrusion can radially extend.

Other types of shape changing protrusions can be provided as well, for example, as described below. In an exemplary embodiment of the invention, the retracting overtube of FIG. 14 is used with the above described protruding anchors. Optionally, the above protrusions are not hollow, but a needle, if provided is narrow enough or has recesses formed therein or is upstream of said protrusions so that the protrusions can be radially compressed into the cannula lumen. In one example, the needle is distal of the protrusions the over tube is retracted before retracting the needle, so the protrusion unblocks the channel. Optionally, anchoring before needle retraction is provided in other embodiments of the invention. Alternatively, in some embodiments, the needle is retracted, at least in part before anchoring (e.g., before completing the advancing of the cannula into the vessel and/or before release of the anchors).

FIGS. 14A-14I illustrate an embodiment where an anchor which is predisposed to radially extend (e.g., by rolling radially away from the cannula and optionally axially towards the cannula) is maintained in a non-extended state by an overtube, and where retraction of the over tube causes deployment of the anchor. In the embodiment shown, the overtube is held in place and the inner tube, a fluid carrying element which also acts as an anchoring element is advanced. In an alternative embodiment, the inner tube is maintained in place (e.g., via an extension outside of the body) and the overtube is retracted.

The inner and outer tubes may be formed, for example, of derivatives of polyurethane, Teflon or polypropylene. In some embodiments the two tubes are of a same material. In other embodiments, the two tubes are of different materials.

Figure 14A:
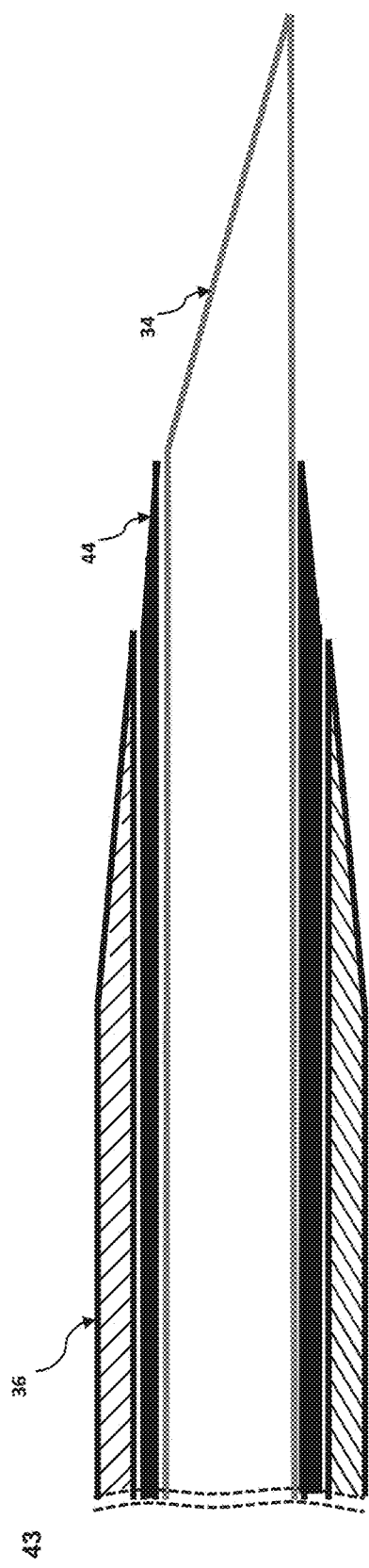
FIG. 14A is a schematic diagram illustrating a cross-sectional side view of an exemplary embodiment of the catheter, including a needle, and a cannula whose invasive section includes an anchoring element associated with the inner surface thereof, e.g., extending from a fluid carrying tube, in accordance with an exemplary embodiment of the present invention.

FIG. 14A is a schematic diagram illustrating a cross-sectional side view of an exemplary embodiment of the catheter 43, including a needle 34, and a cannula 36 whose invasive section includes an anchoring element 44, featuring a 'movable' type structural/functional mode or configuration, extending from a distal end of the cannula, and potentially being described as configured to protrude from, the inner surface thereof. It should be noted that fluid flow is through the anchoring element and not directly in contact with the cannula body. Thus, the fluid carrying conduit of the cannula is integral with the anchor, while the outer body of the cannula serves only to temporarily restrain the fluid carrying portion.

Figure 14B:
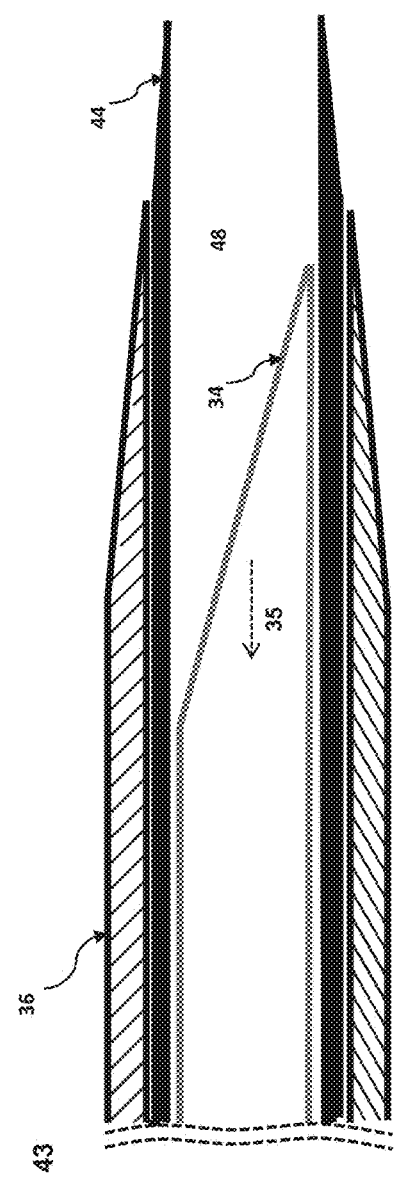
FIG. 14B is a schematic diagram illustrating the same cross-sectional side view shown in FIG. 14A, wherein the needle is being removed from the invasive section of the cannula, in accordance with an exemplary embodiment of the present invention.

FIG. 14B is a schematic diagram illustrating the same cross-sectional side view shown in FIG. 14A, wherein the needle 34 of the catheter 43 is being removed (indicated by the left-directed arrow with reference number 35), through the lumen 48 of the anchoring element 44, from the invasive section of the cannula 36.

Figure 14C:
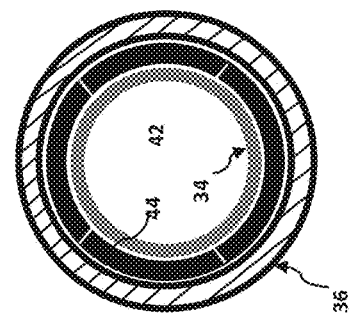
FIG. 14C is a schematic diagram illustrating a cross-sectional front view of the catheter shown in FIGS. 14A and 14B, in accordance with an exemplary embodiment of the present invention.

FIG. 14C is a schematic diagram illustrating a cross-sectional front view of the catheter shown in FIGS. 14A and 14B, showing that the distal end of the cannula is pre-split.

Figure 14E:
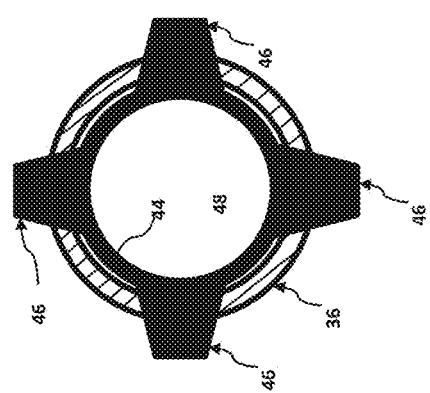
FIG. 14E is a schematic diagram illustrating a cross-sectional front view of the catheter shown in FIG. 14D, in accordance with an exemplary embodiment of the present invention.
Figure 14G:
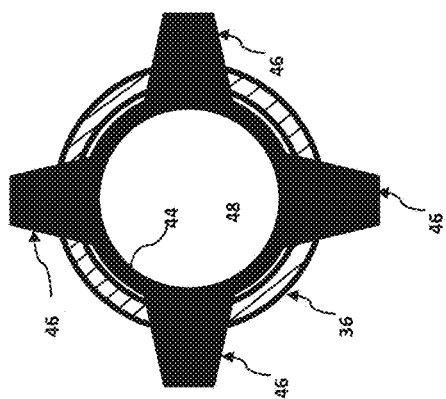
FIGS. 14F and 14G are schematic diagrams respectively illustrating the same cross-sectional side and front views of the catheter shown in FIGS. 14D and 14E, respectively, particularly highlighting additional relative movement such that the external bendable section of the anchoring element further bends open, in accordance with an exemplary embodiment of the present invention.
Figure 14D:
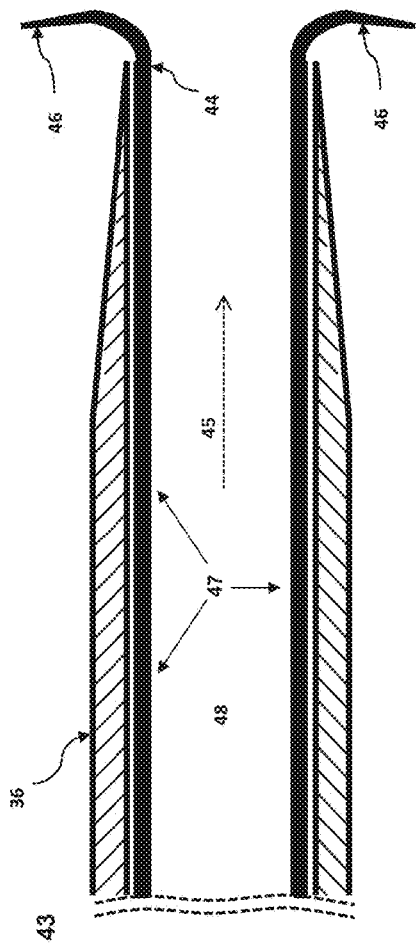
FIG. 14D is a schematic diagram illustrating a cross-sectional side view of the catheter shown in FIGS. 14A, 14B, and 14C, wherein the needle has been removed, and the anchoring element is moved relative to the inner surface of the invasive section of the cannula, such that the external bendable section of the anchoring element starts to bend open, for eventual anchoring of the invasive section of the cannula to a lumen of a body vessel, duct, or cavity, in a treatment space, in accordance with an exemplary embodiment of the present invention.

FIG. 14D is a schematic diagram illustrating a cross-sectional side view of the catheter shown in FIGS. 14A, 14B, and 14C, wherein the needle 34 of the catheter 43 has been removed, and the anchoring element 44 (i.e., via the internal base section 47 thereof) is moved (pushed in the direction towards the tip of the cannula 36; indicated by the right-directed arrow with reference number 45), along the inner surface of the invasive section of the cannula 36, such that the external bendable section 46 of the anchoring element 44 starts to bend open, for eventual anchoring of the invasive section of the cannula 36 to a wall of a body vessel, duct, or cavity, in a treatment space. In an exemplary embodiment of the invention, bendable section 46 is predisposed, for example, by being manufactured or later treated, to curl outwards. Optionally or alternatively, one or more metal wires, for example a super-elastic material are embedded in the bendable sections so as to cause such rolling. In another example, heat or chemical treatment of the outer surface of the bendable sections causes the outer surface to shrink slightly and provide the predisposition for bending or curling. In another example, the tube is formed with the bendable sections bent and they are flattened for insertion into the overtube.

FIG. 14E is a schematic diagram illustrating a cross-sectional front view of the catheter shown in FIG. 14D.

Figure 14F:
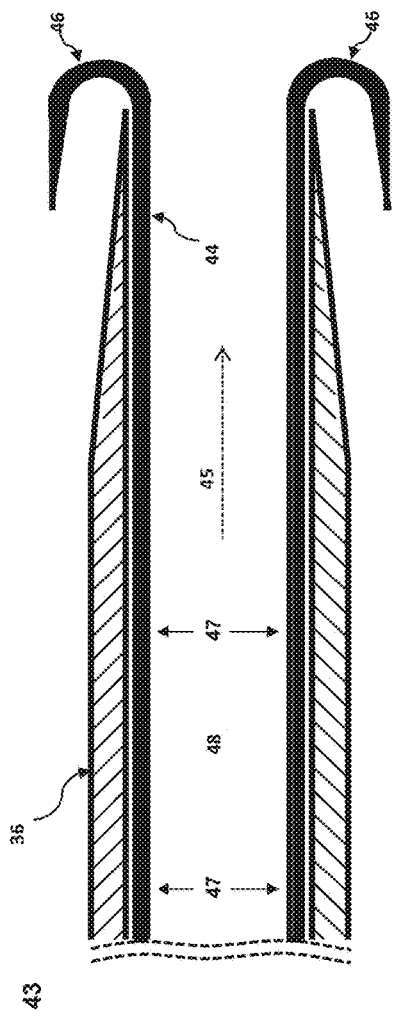

FIGS. 14F and 14G are schematic diagrams respectively illustrating the same cross-sectional side and front views of the catheter 43 shown in FIGS. 14D and 14E, respectively, particularly highlighting additional moving (pushing in the direction towards the tip of the cannula 36; indicated by right-directed arrow 45), such that the external bendable section 46 of the anchoring element 44 further bends open (e.g., to a semi-opened or partially-opened position), for eventual anchoring of the invasive section of the cannula 36 to a wall of a body vessel, duct, or cavity, in a treatment space.

Figure 14I:
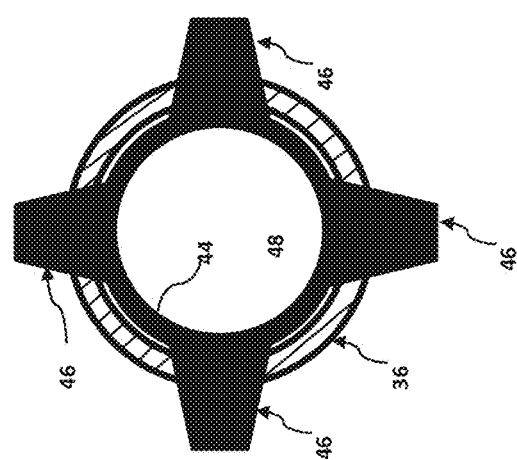
FIGS. 14H and 14I are schematic diagrams respectively illustrating the same cross-sectional side and front views of the catheter shown in FIGS. 14F and 14G, respectively, particularly highlighting further additional relative moving, such that the external bendable section of the anchoring element even further bends open (e.g., to a fully-opened position), for anchoring of the invasive section of the cannula to a wall of a body vessel, duct, or cavity, in a treatment space, in accordance with an exemplary embodiment of the present invention.
Figure 14H:
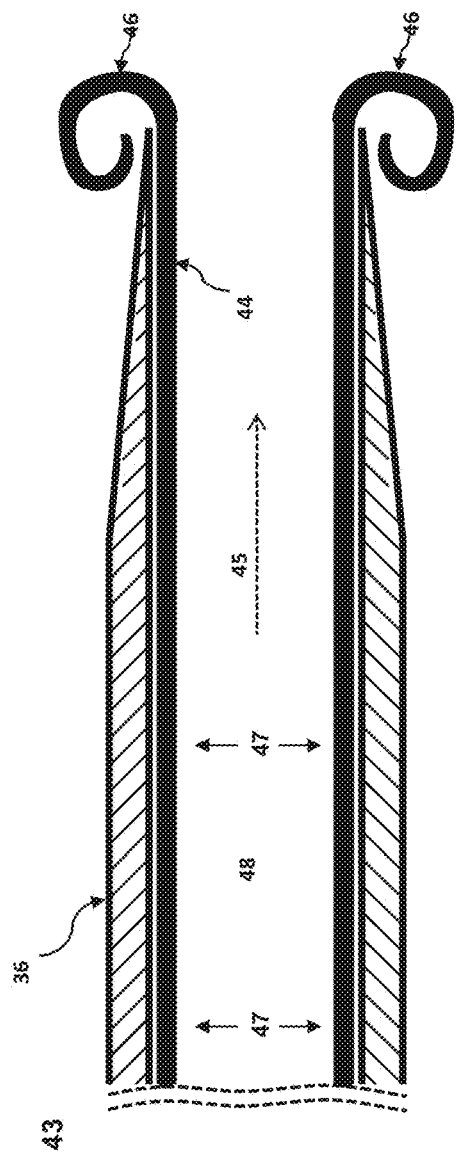

FIGS. 14H and 14I are schematic diagrams respectively illustrating the same cross-sectional side and front views of the catheter 43 shown in FIGS. 14F and 14G, respectively, particularly highlighting a final anchoring state resulting from completing the movement It should be noted that in other embodiments, relative motion of cannula outer body 36 and anchoring element tube 44 are achieved by retraction of the cannula body, rather than or in addition to advancing of the inner tube.

As noted above, it is a particular feature of some embodiments of the invention that the same tube used to carry fluid also acts as an anchoring element by including or having an integrally formed or mounted protrusion.

Figure 15:
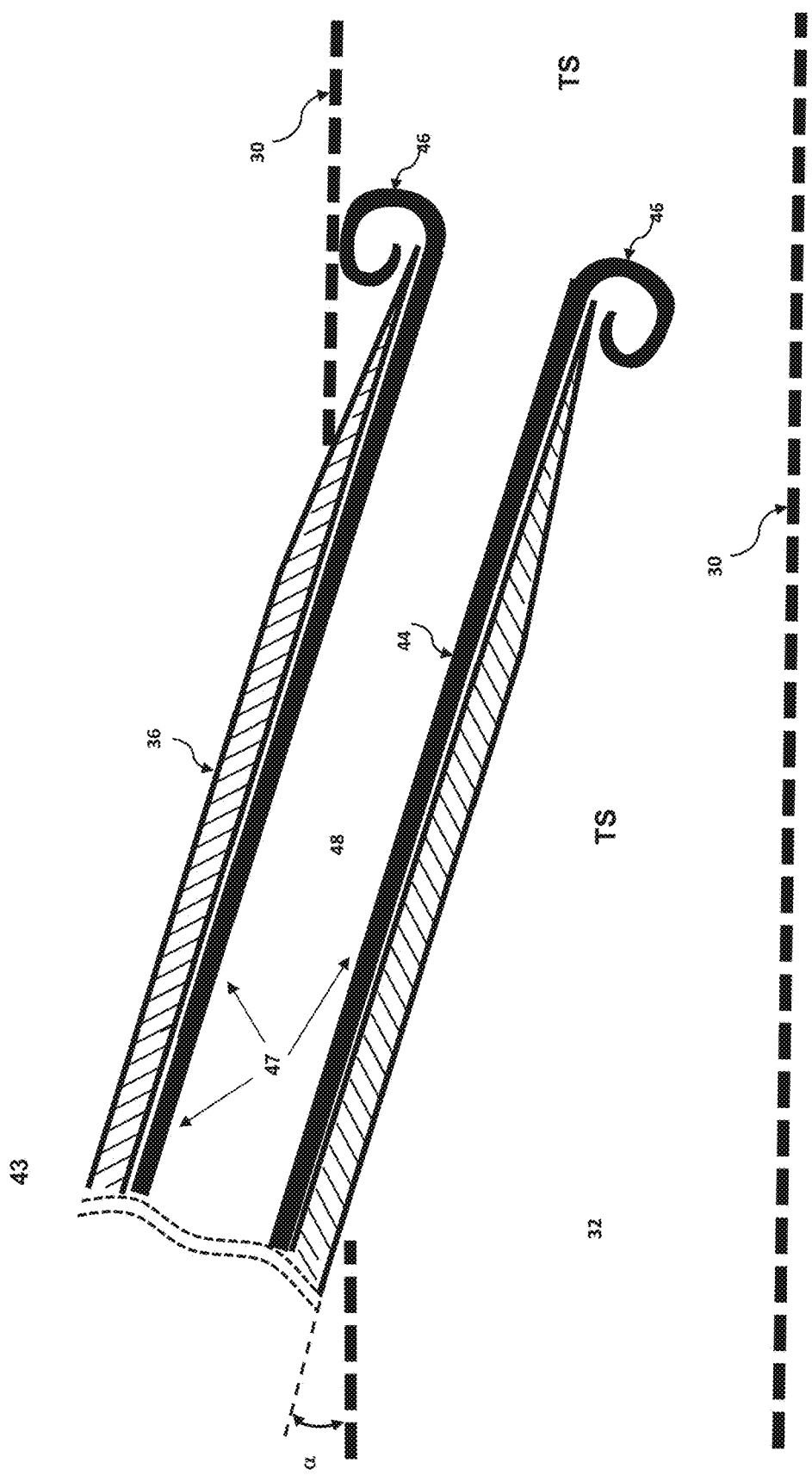
FIG. 15 is a schematic diagram illustrating a cross-sectional side view of the catheter shown in FIGS. 14H-I, wherein the needle has been removed, and the invasive section of the cannula is inserted into a treatment space of a body vessel, duct, or cavity, particularly highlighting exemplary operative location, position, and configuration of the anchoring element within the treatment space, and highlighting the angle (α) [e.g., 10-45°] in which the invasive section of the cannula is inserted into the treatment space, in accordance with an exemplary embodiment of the present invention.

FIG. 15 is a schematic diagram illustrating a cross-sectional side view of the catheter shown in FIGS. 14H-I, wherein the needle 34 of the catheter 43 has been removed, and the invasive section of the cannula 36 is inserted into a treatment space TS within a lumen 32 of a body vessel, duct, or cavity, particularly highlighting operative location, position, and configuration of the anchoring element external bendable section 46 (contacting, and anchoring the invasive section to, a vessel, duct, or cavity, wall) within the treatment space TS, and highlighting the angle ($\alpha$) [e.g., 10-45°] in which the invasive section of the cannula 36 is inserted into the treatment space TS.

In an exemplary embodiment of the invention, bendable section 46 acts as a spring to flexibly react to mechanical forces. Optionally, if the vein collapses or the catheter is moved and/or retracted, the contact of the anchoring element and/or of the cannula with the wall is mediated by the spring effect.

Another potential advantage is that upon inadvertent retraction, the spring cushions the contact with the area around the aperture in the vessel. A protrusion of the type of FIG. 7A, for example, might cause some radial force to be applied on the aperture, but a rolled up edge, according to some embodiments of the invention, might first apply an axial resistance before any radial force is applied.

A potential advantage of using a curling tip (e.g., curling more than about 270 degrees, is that there need be no sharp edges in contact with the vessel wall. Optionally, the side edges (e.g., the upper angular points as shown in each of the four flaps in FIG. 14E) of the bending sections are smoothed and/or rounded, to reduce the occurrence of sharp edges. In some embodiments, instead of curling, only outwards bending of one or more extensions is provided. Such an extension (or a curling extension or other extension type) can extend from, for example, 5%, 10%, 20%, 40% or smaller or intermediate percentages of the circumference of the cannula.

Figure 16:
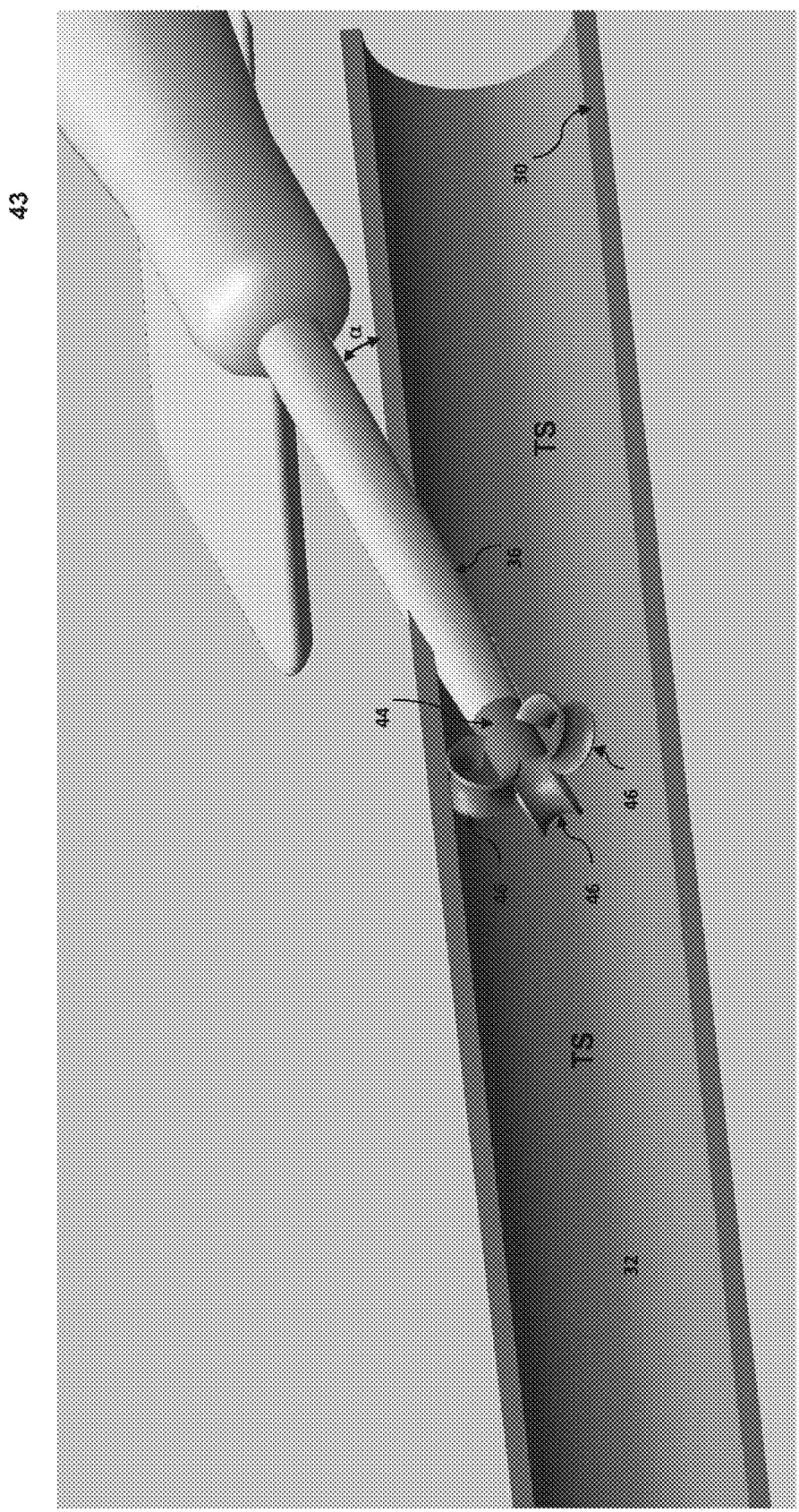
FIG. 16 is a pictorial diagram illustrating a perspective view of the catheter shown in FIG. 15, wherein the needle has been removed, and the invasive section of the cannula is inserted into a treatment space of a body vessel, duct, or cavity, particularly highlighting operative location, position, and configuration of the anchoring element within the treatment space, and highlighting the angle (α) [e.g., 10-45°] in which the invasive section of the cannula is inserted into the treatment space, in accordance with an exemplary embodiment of the present invention.

FIG. 16 is a pictorial diagram illustrating a perspective view of the catheter 43 shown in FIG. 15, wherein the needle 34 has been removed, and the invasive section of the cannula 36 is inserted into the treatment space TS within the lumen 32 of the body vessel, duct, or cavity, particularly highlighting operative location, position, and configuration of the anchoring element (contacting, and anchoring the invasive section to, a vessel, duct, or cavity, wall) within the treatment space, and highlighting the angle ($\alpha$) [e.g., 10-34°] in which the invasive section of the cannula 36 is inserted into the treatment space TS. It should be noted that FIG. 16 shows a cannula design with three rolled back anchoring portions. A smaller or larger number may be provided, for example, 1, 2, 4 or more. The above noted radial dimension of a protrusion may apply, for example, to a single protrusion or to all the protrusions taken together.

Optionally, rotation of the anchoring element may be used to assist in withdrawal thereon and/or retraction of the cannula from the body. Such rotation may be provided, for example, by the design shown in FIG. 17A.

Figure 17A:
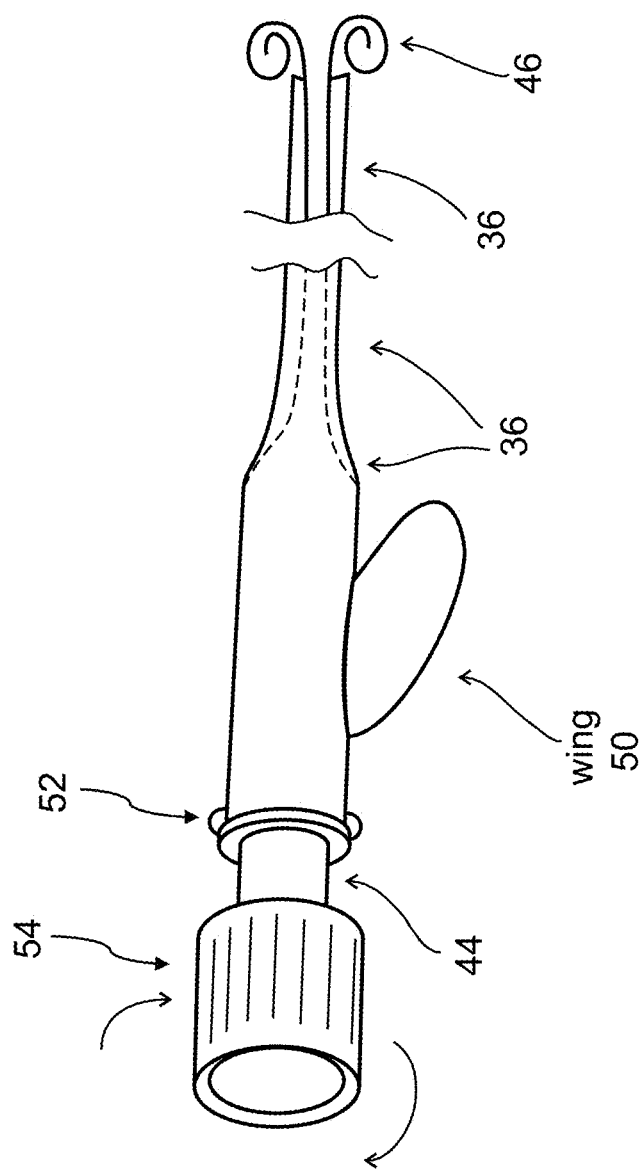
FIGS. 17A and 17B illustrate a locking mechanism for locking inner and outer tubes of a vascular port using the mechanism of FIGS. 14-16, in accordance with an exemplary embodiment of the invention.
Figure 17B:
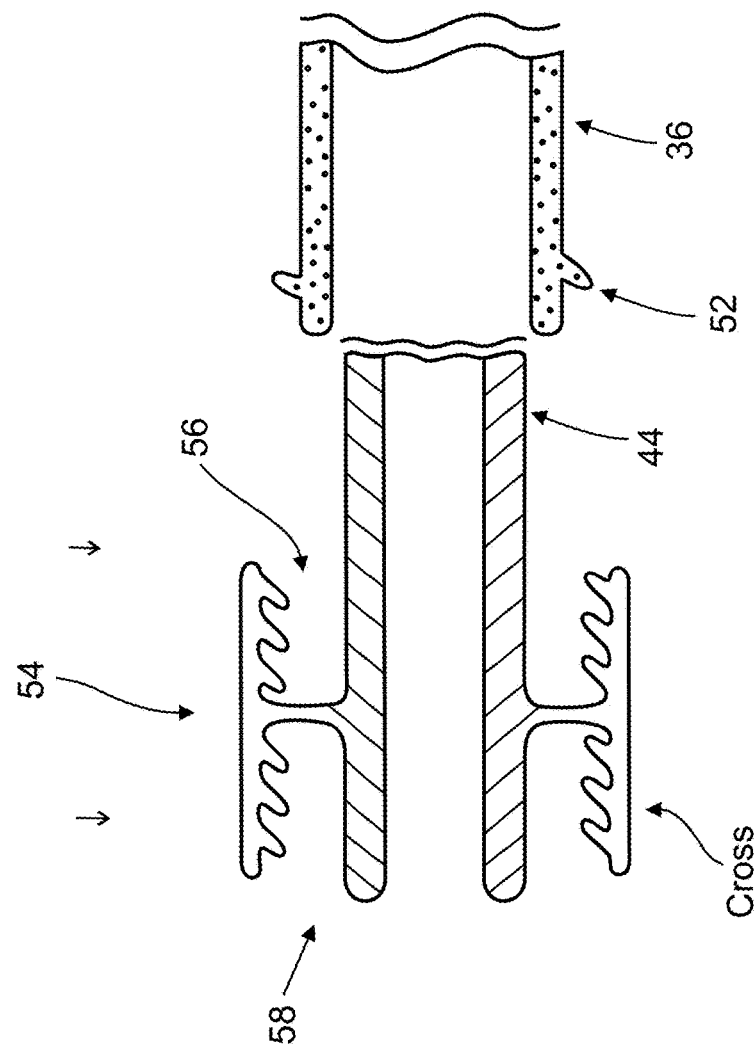

FIGS. 17A and 17B illustrate, in side view and side-cross-sectional view, a locking mechanism for locking inner and outer tubes of a vascular port using the mechanism of FIGS. 14-16, in accordance with an exemplary embodiment of the invention. In the example shown, a Luer lock 54 is coupled to anchoring element tube 44 and can be selectively locked to a protrusion or thread 52 that is coupled to cannula outer body tube 36. Also shown is an optional wing 50 for fixation to the skin. In an exemplary embodiment of the invention, the length of travel of the tubes and the Luer lock is selected so that a same motion advances the inner tube and locks the two tubes together and an opposite motion unlocks the tubes and causes a relative retraction of the inner tube. In an alternative embodiment, the tube is fully advanced before being locked and is first unlocked and only then retracted enough to uncouple the anchoring.

In the embodiment shown the Luer lock 54 is female both for locking to the tube and for attachment to other medical equipment. Alternatively, a proximal side 58 of the Luer lock is of a different design, or omitted, to support other method of attachment to medical equipment. A distal side 56 of the Luer lock is shown to be of a female type, but it could be male or a different locking mechanism for the outer cannula tube provided, for example, a slip ratchet, or an interference snap fit.

It should be noted that some of the devices for example those described in U.S. Pat. No. 5,256,146 and in U.S. Pat. No. 5,509,900 use anchoring mechanisms that are based on features that activates pressure on the vessel wall, and therefore may increase the irritation.

Some embodiments of the present invention exhibit a simple anchoring mechanism where the anchor elements may be fixed to the cannula and therefore may not increase the product costs. Moreover, the manipulation of the catheter can remain standard or near standard. It should be noted that peripheral infusion catheters are cheap disposable products, and therefore any complication of their mechanism may significantly increase their cost and this may be avoided in accordance with some embodiments of the invention. In addition, the catheter manipulation gets more complex and requires more skills and training when the anchoring mechanism is complex and this may be avoided in accordance with some embodiments of the invention.

It should be noted that, in some embodiments of the invention, not only can the catheter flow cross-section stay the same or nearly the same, due to the decrease in the cannula's length, the resistance of the cannula to flow reduces; meaning that higher maximal flow rates may be achieved, or alternatively, smaller diameter catheters may be used for the same required flow rates.

It is expected that during the life of a patent maturing from this application many relevant methods and systems will be developed and the scope of the terms cannula, protrusions and catheter are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The term 'method', as used herein, refers to manners, means, techniques, or/and procedures, for accomplishing a given task including, but not limited to, those manners, means, techniques, or/and procedures, either known to, or readily developed from known manners, means, techniques, or/and procedures, by practitioners in the relevant field(s) of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A cannula for fluid exchange with a body lumen, the cannula comprising:
    an elongated flexible tube having a single distal aperture, said elongate flexible tube coupleable to a needle such that said elongated flexible tube concentrically surrounds the needle, and having an invasive section and a non-invasive section and defining a lumen for fluid transfer; and
    at least one anchoring element integral with said tube invasive section and permanently radially extending away from said tube, said tube having said at least one radially extending anchoring element extending away from an outermost surface of said tube invasive section adapted to be inserted into the body lumen when said at least one radially extending anchoring element extends away from said tube and said at least one anchoring element adapted to contact an inner wall of the body lumen, each of said at least one anchoring element configured for contacting the inner wall of the body lumen without damaging the inner wall of the body lumen, wherein said invasive section and said at least one anchoring element are formed from a single piece;
    wherein a wall of said elongate flexible tube has a first thickness at a portion of said wall without one of said at least one anchoring elements and has a second thickness at a portion of said wall from which one of said at least one anchoring elements protrudes, said second thickness being greater than said first thickness; and
    wherein each of said at least one anchoring element includes a leading edge and a trailing edge sloping away in a proximal direction from said leading edge.

2. The cannula according to claim 1, wherein said radial extension is less than 30% of an outer diameter of said tube other than at an anchoring element location.

3. The cannula according to claim 1, wherein said radial extension is less than 50% of an outer diameter of said tube other than at an anchoring element location.

4. The cannula according to claim 1, wherein said at least one anchoring element is narrowing toward a front portion of said anchoring element.

5. The cannula according to claim 1, wherein said at least one anchoring element comprises a first anchoring element closer to a tip of said cannula and a second anchoring element further from said tip of said cannula.

6. The cannula according to claim 1, wherein a ratio between an outer diameter of said elongated flexible tube and length of said invasive section is at least 0.07.

7. The cannula according to claim 1, wherein said invasive section has a first effective diameter relative to an aperture in the body lumen when inserted into the body lumen and wherein said invasive section is configured to have a second effective diameter relative to the aperture in the body lumen, said second effective diameter smaller than said first effective diameter when said invasive section is removed from the body lumen.

8. The cannula according to claim 7, wherein said invasive section is configured to have said second effective diameter smaller than said first effective diameter when said invasive section is one of turned and twisted about an axis of said cannula.

9. The cannula according to claim 1, wherein said at least one anchoring element comprises a pair of anchoring elements, and wherein the relative positions of said pair of anchoring elements along said tube are selected such that an angle between a line connecting said anchoring elements and an axis of said cannula matches an expected insertion angle of said cannula into the body lumen.

10. The cannula according to claim 9, wherein said non-invasive section is provided with markings for indicating an orientation for insertion of said cannula into the body lumen.

11. The cannula according to claim 1, wherein said at least one anchoring element comprises a single anchoring element.

12. The cannula according to claim 1, wherein each said at least one anchoring element includes a protrusion protruding from an outer surface of said invasive section.

13. The cannula according to claim 12, wherein said protrusion includes said leading edge, wherein said protrusion is narrowest at a tip of said leading edge.

14. The cannula according to claim 12, wherein said protrusion includes said trailing edge, wherein said protrusion is widest at a tip of said trailing edge.

15. The cannula according to claim 1, wherein said at least one anchoring element includes at least two protrusions, and wherein two of said at least two protrusions are configured to trap a vessel wall and skin between said at least two protrusions when said cannula is inserted in the body lumen.

16. The cannula according to claim 1, wherein said at least one anchoring element comprises a hollow element.

17. The cannula according to claim 16, wherein said at least one anchoring element is formed by one of heat-working, mold-injection, extrusion of said cannula tube, and a combination thereof.

18. The cannula according to claim 1, wherein said tube and said at least one anchoring element are made of a single material.

19. The cannula according to claim 1, wherein said at least one anchoring element is configured to prevent damage to a wall of the body lumen.

20. The cannula according to claim 1, wherein said single distal aperture is configured for fluid exchange with the body lumen.

21. The cannula according to claim 1, wherein said at least one anchoring element includes a pair of anchoring elements which are diametrically oppositely positioned relative to each other on said outermost surface of said invasive section.

22. The cannula according to claim 1, wherein said at least one anchoring element includes a pair of anchoring elements which are diagonally oppositely positioned relative to each other on said outermost surface of said invasive section.

23. The cannula according to claim 1, wherein said trailing edge has at least one of a greater slope and a width at least as wide at a tip of said trailing edge as a widest part of a leading section.

24. The cannula according to claim 1, wherein said at least one anchoring element has a rounded edge.

25. The cannula according to claim 1, wherein said preventing damage includes not piercing the vessel wall.

26. The cannula according to claim 1, wherein each of said at least one anchoring element includes a protrusion having said leading edge and said trailing edge, said leading edge extending from a widest point on said protrusion to a most distal portion of said protrusion, said trailing edge extending from a widest point on said protrusion to a most proximal portion of said protrusion.

27. The cannula according to claim 1, wherein a leading angle is selected from a range of from 5-40 degrees, said leading angle defined as an angle between said leading edge and an outer surface of said tube proximal to said leading edge.

28. The cannula according to claim 1, wherein a trailing angle is selected from 60 degrees, 90 degrees, and 120 degrees, said trailing angle defined as an angle between said trailing edge and an outer surface of said tube proximal to said trailing edge.

29. The cannula according to claim 1, wherein said trailing edge has at least one of an angle and a geometry configured to match an expected angle of said trailing edge with the inner wall of the body lumen.

30. The cannula according to claim 1, wherein a slope of each of said leading and trailing edges is less than 90 degrees, wherein said slope of said leading edge is defined as an angle between said leading edge and an outer surface of said tube proximal to said leading edge, and wherein said slope of said trailing edge is defined as an angle between said trailing edge and an outer surface of said tube distal to said trailing edge.

31. The cannula according to claim 1, wherein each of said at least one anchoring element slopes up and then slopes down, in an axial direction from said leading edge to said trailing edge.

32. The cannula according to claim 1, wherein said at least one anchoring element provides an increase in maximum diameter to said tube of up to 50%.

33. The cannula according to claim 1, wherein said tube has a uniform inner diameter at an anchoring element location and at a distal end of said tube.

34. A method of fluid exchange with a body lumen, comprising:
inserting at least part of an invasive section of a cannula into said lumen via an aperture into a treatment space, wherein said cannula is configured as an elongated flexible tube having a single distal aperture, said cannula configured to concentrically surround a needle, said elongated flexible tube having an invasive section and a non-invasive section, and having at least one anchoring element integral with said invasive section and permanently radially extending away from said tube, said tube having said at least one radially extending anchoring element extending away from an outermost surface of said tube invasive section adapted to be inserted into the body lumen when said at least one radially extending anchoring element extends away from said tube, wherein said at least one anchoring element and said invasive section are formed from a single piece, wherein each of said at least one anchoring element includes a leading edge and a trailing edge sloping away in a proximal direction from said leading edge, wherein a wall of said elongate flexible tube has a first thickness at a portion of said wall without one of said at least one anchoring elements and has a second thickness at a portion of said wall from which one of said at least one anchoring elements protrudes, said second thickness being greater than said first thickness;
preventing retraction of said cannula from said aperture by said anchoring element mechanically contacting an inner wall of the body lumen and interfering with said aperture without damaging the inner wall of the body lumen; and
administering a fluid or/and substance to, or draining the fluid or/and substance from, the treatment space of the body vessel, duct, or cavity, via said cannula.

35. The method of claim 34, wherein said inserting and said preventing comprise not allowing said cannula to have an outer diameter equal to or greater than said vessel.

36. The method of claim 34, wherein said inserting and said preventing comprise not allowing said cannula to have an outer diameter greater than 130% of an inner diameter thereof.

37. The method of claim 34, wherein said lumen is a vein lumen and wherein said inserting and said preventing comprise avoiding contacting a wall of said vein that is opposite said aperture.

38. The method of claim 34, wherein the elongated flexible tube has a first diameter, said method further comprising performing an act which causes the cannula invasive section to have a second diameter smaller than said first diameter, thereby allowing retraction of the cannula from the aperture.

39. The method of claim 38, wherein said performing includes one of turning and twisting the cannula invasive section about an axis of the cannula.

40. A cannula for fluid exchange with a body lumen, the cannula comprising:
an elongated flexible tube having a single distal aperture, said elongate flexible tube coupleable to a needle such that said elongated flexible tube concentrically surrounds the needle, and having an invasive section and a non-invasive section and defining a lumen for fluid transfer; and
at least one anchoring element integral with said tube invasive section and permanently radially extending away from said tube, said tube having said at least one radially extending anchoring element extending away from an outermost surface of said tube invasive section adapted to be inserted into the body lumen when said at least one radially extending anchoring element extends away from said tube and said at least one anchoring element adapted to contact an inner wall of the body lumen, each of said at least one anchoring element configured for contacting the inner wall of the body lumen without damaging the inner wall of the body lumen, wherein said at least one anchoring element and said invasive section are integrally formed;
wherein a wall of said elongate flexible tube has a first thickness at a portion of said wall without said at least one anchoring element and has a second thickness at a portion of said wall from which said at least one anchoring element protrudes, said second thickness being greater than said first thickness; and
wherein each of said at least one anchoring element includes a leading edge and a trailing edge sloping away in a proximal direction from said leading edge.

* * * * *